US010126211B2

(12) United States Patent
Yamakawa et al.

(10) Patent No.: US 10,126,211 B2
(45) Date of Patent: Nov. 13, 2018

(54) BODILY FLUID SAMPLER

(71) Applicants: Masami Yamakawa, Yamanashi (JP); Miyuki Yamakawa, Yamanashi (JP)

(72) Inventors: Masami Yamakawa, Yamanashi (JP); Miyuki Yamakawa, Yamanashi (JP)

(73) Assignee: Miyuki Yamakawa, Yamanashi (JP)

( * ) Notice: Subject to any disclaimer, the term of this patent is extended or adjusted under 35 U.S.C. 154(b) by 312 days.

(21) Appl. No.: 15/058,099

(22) Filed: Mar. 1, 2016

(65) Prior Publication Data
US 2016/0245729 A1 Aug. 25, 2016

Related U.S. Application Data

(63) Continuation of application No. PCT/JP2014/073363, filed on Sep. 4, 2014.

(30) Foreign Application Priority Data

Sep. 5, 2013 (JP) .................... 2013-183901
Dec. 2, 2013 (JP) .................... 2013-248855
Jul. 23, 2014 (JP) .................... 2014-150113

(51) Int. Cl.
A61B 10/00 (2006.01)
G01N 1/14 (2006.01)
(Continued)

(52) U.S. Cl.
CPC ......... *G01N 1/14* (2013.01); *A61B 5/150022* (2013.01); *A61B 5/150343* (2013.01);
(Continued)

(58) Field of Classification Search
CPC .................................................. A61B 10/00
See application file for complete search history.

(56) References Cited

U.S. PATENT DOCUMENTS 3,610,242 A * 10/1971 Sheridan ............. A61M 1/0047
600/579
4,396,024 A 8/1983 Sarstedt
(Continued)

FOREIGN PATENT DOCUMENTS

CN 1988924 A 6/2007
DE 202004004951 U1 8/2004
(Continued)

OTHER PUBLICATIONS

International preliminary report on patentability for PCT/JP2014/073363 dated Mar. 17, 2016.
(Continued)

*Primary Examiner* — Robert R Raevis
(74) *Attorney, Agent, or Firm* — Basil M. Angelo; Angelo Mikeska PLLC

(57) ABSTRACT

A bodily fluid sampler includes a suction part that sucks the bodily fluid, a main body part that includes a ventilation channel which allows gas for discharging the bodily fluid sucked by the suction part to pass therethrough, and a blocking part that is provided between the main body part and the suction part, and the blocking part preventing the bodily fluid sucked by the suction part from flowing into the main body part. An inner diameter of the opening part formed in the blocking part is smaller than an inner diameter of the suction part at a surface where the suction part and the blocking part make contact with each other, and thus, the bodily fluid is prevented from being sucked by the suction part more than a predetermined amount.

6 Claims, 21 Drawing Sheets

(51) Int. Cl.
*A61B 5/15* (2006.01)
*B01L 3/02* (2006.01)
*B01L 3/00* (2006.01)

(52) U.S. Cl.
CPC .......... *A61B 10/0045* (2013.01); *B01L 3/021* (2013.01); *A61B 10/007* (2013.01); *B01L 3/0275* (2013.01); *B01L 3/5021* (2013.01); *B01L 2300/043* (2013.01); *B01L 2300/048* (2013.01); *B01L 2400/0481* (2013.01)

(56) References Cited

U.S. PATENT DOCUMENTS

| | | | | |
|---|---|---|---|---|
| 4,436,098 | A | * 3/1984 | Kaufman | A61B 5/15003 600/579 |
| 4,942,966 | A | 7/1990 | Kemp | |
| 5,052,403 | A | * 10/1991 | Haber | A61B 5/15003 600/578 |
| 5,257,984 | A | 11/1993 | Kelley | |
| 5,834,272 | A | 11/1998 | Righetti | |
| 5,873,841 | A | * 2/1999 | Brannon | A61B 5/15003 600/578 |
| 5,897,508 | A | * 4/1999 | Konrad | A61B 5/15003 600/573 |
| 6,024,138 | A | 2/2000 | Fritz et al. | |
| 6,641,993 | B1 | * 11/2003 | Jacobs | B01F 5/10 366/305 |
| 8,460,617 | B2 | * 6/2013 | Schacher | B01L 3/0275 422/524 |
| 2002/0076826 | A1 | * 6/2002 | Jacobs | B01F 5/10 436/174 |
| 2002/0134175 | A1 | * 9/2002 | Mehra | B01L 3/0275 73/863.85 |
| 2003/0139688 | A1 | * 7/2003 | Lamoureux | A61B 10/025 600/578 |
| 2005/0245868 | A1 | 11/2005 | Brown | |
| 2005/0245869 | A1 | 11/2005 | Brown | |
| 2007/0106220 | A1 | 5/2007 | Brown | |
| 2008/0237115 | A1 | 10/2008 | Shintani et al. | |
| 2009/0177116 | A1 | * 7/2009 | Nakaminami | A61B 10/0045 600/573 |
| 2010/0009832 | A1 | 1/2010 | Schaefer et al. | |

FOREIGN PATENT DOCUMENTS

| | | |
|---|---|---|
| JP | 5568357 A | 5/1980 |
| JP | 8108096 A | 4/1996 |
| JP | H09141135 | 6/1997 |
| JP | 1111513 U | 1/1999 |
| JP | 2004321905 A | 11/2004 |
| JP | 2005017280 A | 1/2005 |
| JP | 2008237310 A | 10/2008 |
| JP | 2009510398 A | 3/2009 |
| WO | 9407764 A1 | 4/1994 |
| WO | 2005094681 A1 | 10/2005 |

OTHER PUBLICATIONS

International search report for PCT/JP2014/073363 dated Dec. 9, 2014.
Extended European Search Report and European Search Opinion for EP14841698 (PCT/JP2014/073363) dated Jun. 13, 2017.
Chinese Office Action for corresponding Chinese application 201480049024.4, dated Jun. 20, 2017.
Korean Office Action for corresponding Korean application 10-2016-7005787, dated Jul. 3, 2017.

* cited by examiner

BODILY FLUID SAMPLER

CROSS-REFERENCE TO RELATED APPLICATIONS

This application is a continuation of PCT International Application PCT/JP2014/073363, filed on Sep. 4, 2014, which claims priority to Japanese Patent Application JP2014-150113, filed on Jul. 23, 2014, Japanese Patent Application JP2013-248855, filed on Dec. 2, 2013, and Japanese Patent Application JP2013-183901, filed on Sep. 5, 2013, all of which are hereby incorporated by reference in their entirety.

BACKGROUND OF THE INVENTION

The present invention relates to a bodily fluid sampler for sampling a bodily fluid, a bodily fluid container for accommodating a bodily fluid or a chemical solution, and a bodily fluid sampling device.

Bodily fluid samplers for sampling a bodily fluid, such as blood and urine or the like, to be used in examinations for making diagnoses on people's health conditions have been conventionally known (see, for example, JP2005-017280A). An absorber (for example, absorbent fiber), which is a collection of fibers that can absorb a bodily fluid through contact with the bodily fluid, is provided in conventional bodily fluid samplers, and the bodily fluid is sampled by a user who samples the bodily fluid and causes the bodily fluid to be absorbed into the ab sorb er.

When the bodily fluid absorbed by the absorber is blood, blood plasma may be separated by applying pressure onto a cylinder provided with a filtration membrane in a blood plasma separator, under the condition in which the absorber is immersed in a separator liquid in the blood plasma separator.

BRIEF SUMMARY OF THE INVENTION

However, when the bodily fluid is caused to be absorbed by the absorber, the amount of the bodily fluid that has been absorbed in the absorber has been unavailable to the user. For example, when blood is absorbed in the absorber, the user was able to know the approximate amount of the absorbed blood based on a color change in the absorber; however, it has been difficult to know the absorbed amount in high precision. Accordingly, when a bodily fluid is sampled by means of conventional bodily fluid samplers, variations occurred in the bodily fluid sampling amounts, and therefore, there existed a problem to the effect that variations also occurred in the result of the examination using such sampled bodily fluid.

In addition, when component separation is carried out on the bodily fluid absorbed in the absorber, the bodily fluid sometimes deteriorates in the process of separation. For example, when blood plasma separation is carried out with the blood absorbed in the absorber, the blood plasma within the blood is destroyed, and therefore, there existed a problem to the effect that the accuracy of the blood examination result is also decreased.

Accordingly, the present invention has been made in view of these points, and an object thereof is to provide a bodily fluid sampler that is capable of sampling a desired amount of bodily fluids without using an absorber.

A bodily fluid sampler according to the present invention comprises: a suction part that sucks a bodily fluid; a main body part that includes a ventilation channel which allows gas for discharging the bodily fluid sucked by the suction part to pass therethrough; and a blocking part that is provided between the main body part and the suction part, and the blocking part preventing the bodily fluid sucked by the suction part from flowing into the main body part.

An inner diameter of the opening part formed in the blocking part is smaller than an inner diameter of the suction part at a surface where the suction part and the blocking part make contact with each other. The bodily fluid sampler provided with such configuration is capable of preventing the bodily fluid from being sucked by the suction part more than a predetermined amount.

DETAILED DESCRIPTION OF THE INVENTION

<Summary of the Disclosure>

Figure 1:
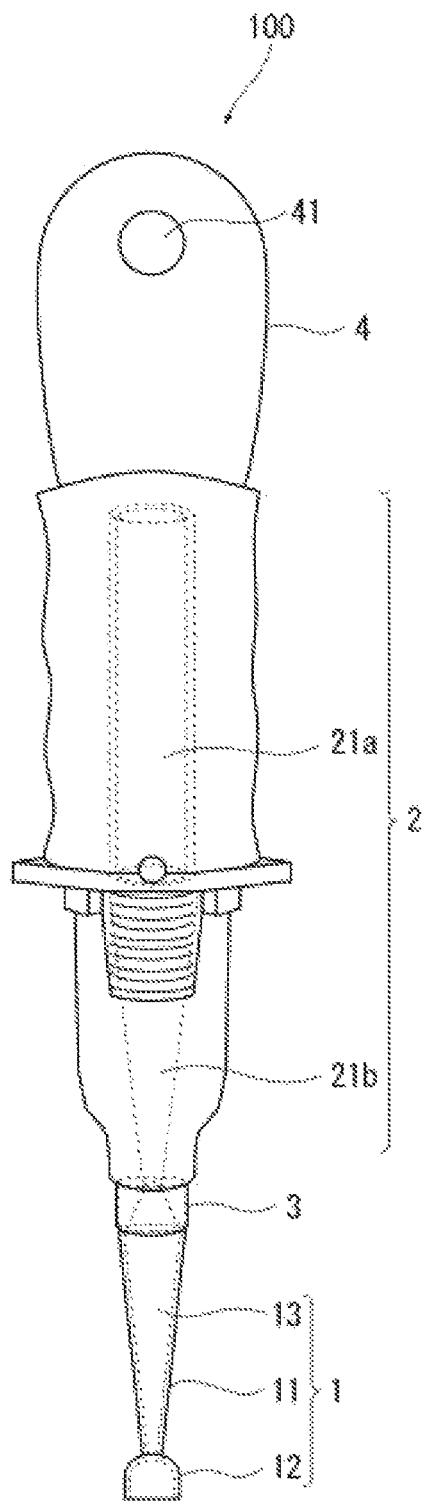
FIG. 1 is a diagram showing a configuration of a bodily fluid sampler according to a first embodiment.

A bodily fluid sampler according to a first embodiment of the present invention comprises: a suction part that sucks a bodily fluid; a main body part that includes a ventilation channel which allows gas for discharging the bodily fluid sucked by the suction part to pass therethrough; and a blocking part that is provided between the main body part and the suction part, the blocking part being formed with an opening part in a tapered form, with an inner diameter thereof on the main body part side being smaller than an inner diameter thereof on the suction part side, and the blocking part preventing the bodily fluid sucked by the suction part from flowing into the main body part. An inner diameter of the opening part formed in the blocking part is smaller than an inner diameter of the suction part at a surface where the suction part and the blocking part make contact with each other. The bodily fluid sampler provided with such configuration is capable of preventing the bodily fluid from being sucked by the suction part more than a predetermined amount.

The above-described bodily fluid sampler may further comprise a pressure generating part that generates a pressure for moving the gas for discharging the bodily fluid toward the suction part.

In addition, the ventilation channel provided to the main body part has, for example, a smallest inner diameter at a surface where the main body part and the blocking part make contact with each other. Moreover, an inner diameter of the ventilation channel has, for example, a size equal to or larger than that of the inner diameter of the opening part at a surface where the main body part and the blocking part make contact with each other.

An outer diameter of the blocking part may be smaller than an inner diameter of the suction part at a position where the suction part makes contact with the main body part, and the blocking part may be provided on an inner side of the suction part. The suction part may be connected to the main body part, in a detachable manner, in the state in which the blocking part is provided on the inner side of the suction part.

A bodily fluid container according to a second embodiment of the present invention comprises: an inner accommodating part that includes an inner cavity part being capable of accommodating a bodily fluid sampled by a bodily fluid sampler; an inner lid part that closes off the inner cavity part of the inner accommodating part; an outer accommodating part that includes an outer cavity part that receives the inner accommodating part; and an outer lid part that closes off the outer cavity part, in the state in which the inner accommodating part is inserted into the outer cavity part, with the inner cavity part being closed off by the inner lid part.

The above-described bodily fluid container may further comprise: a bendable inner coupling part that couples the inner lid part and the inner accommodating part together; and a bendable outer coupling part that couples the outer lid part and the outer accommodating part together.

In addition, the inner accommodating part may include a projection part that projects toward the outer accommodating part in a direction orthogonal to the direction along which the inner accommodating part is inserted into the outer accommodating part, and the outer accommodating part may include a fixing part that fixes the inner accommodating part to the outer cavity part by the fixing part making contact with the projection part.

Moreover, the inner lid part may include a first inner lid part having a thickness corresponding to a width of the projection part and a second inner lid part having a diameter smaller than that of the first inner lid part, and, in the state in which the inner lid part closes off the inner cavity part, the first inner lid part may make contact with the projection part in the inner cavity part and the second inner lid part may be located, with respect to the projection part, on a side of the inner cavity part where the bodily fluid is accommodated.

A bodily fluid sampling device according to a third embodiment of the present invention comprises: a bodily fluid sampler for sampling a bodily fluid; and the above-described bodily fluid container, wherein a distance between a tip of the bodily fluid sampler and a tip of the inner cavity part is larger than a predetermined value in the state in which the bodily fluid sampler is inserted into the inner accommodating part up to a position where the bodily fluid sampler has a diameter larger than an inner diameter of the inner cavity part.

A bodily fluid sampling device according to a fourth embodiment of the present invention comprises: a bodily fluid sampler for sampling a bodily fluid; and the above-described bodily fluid container, wherein the bodily fluid sampler includes a positioning part that determines a position of the bodily fluid sampler by making contact with at least one of the inner accommodating part and the outer accommodating part in the state in which the bodily fluid sampler is inserted into the inner accommodating part, and a distance between a tip of the bodily fluid sampler and a tip of the inner cavity part is larger than a predetermined value in the state in which the bodily fluid sampler is inserted into the inner accommodating part up to a position where the positioning part makes contact with at least one of the inner accommodating part and the outer accommodating part.

In a fifth embodiment of the present invention, a bodily fluid container is provided, which is capable of accommodating a bodily fluid to be subjected to centrifugal separation. Such bodily fluid container comprises: a first accommodating part that includes a first cavity part for accommodating the bodily fluid; a second accommodating part that is attached to the first accommodating part in a detachable manner and that includes a second cavity part for accommodating the bodily fluid together with the first cavity part, an inner diameter of the second cavity part being smaller than an inner diameter of the first cavity part; and a lid part that obstructs an opening of the second accommodating part, which is located on an opposite side from a side where the second accommodating part is attached to the first accommodating part.

The second accommodating part may be press-fitted into and attached to an opening part located on the second accommodating part side of the first accommodating part. The second accommodating part may be made of a material harder than that of the first accommodating part. The first accommodating part may be made of a flexible material.

The second accommodating part is formed in a cylindrical shape, and an accommodating part selected from a small-diameter accommodating part and a large-diameter accommodating part, each of which having a different inner diameter, may be attached, as the second accommodating part, to the first accommodating part. An outer diameter of the large-diameter accommodating part may have a size the same as an outer diameter of the small-diameter accommodating part.

The bodily fluid is blood containing blood plasma and blood cells, and after the bodily fluid is subjected to centrifugal separation, the first accommodating part may accommodate the blood plasma and the second accommodating part may accommodate the blood cells. The first accommodating part and the second accommodating part are capable of accommodating a separating agent, and after the bodily fluid is subjected to centrifugal separation, the separating agent may be located at a position connecting the first cavity part and the second cavity part.

In a sixth embodiment of the present invention, a bodily fluid container is provided, which comprises: an inner container capable of accommodating a bodily fluid to be subjected to centrifugal separation; and an outer container that receives the inner container. The inner container includes: a first accommodating part having a first cavity part for accommodating the bodily fluid; a second accommodating part that is attached to the first accommodating part in a detachable manner and that includes a second cavity part for accommodating the bodily fluid together with the first accommodating part, an inner diameter of the second cavity part being smaller than an inner diameter of the first cavity part; and a lid part that obstructs an opening of the second accommodating part, which is located on an opposite side from a side where the second accommodating part is attached to the first accommodating part.

<First Embodiment>

Figure 2:
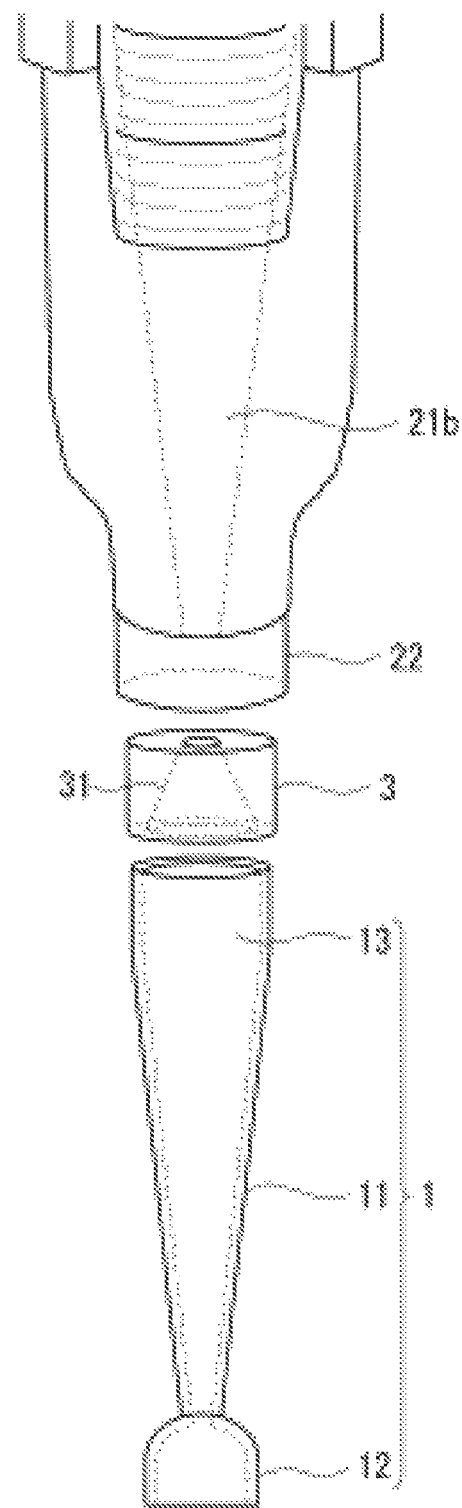
FIG. 2 is a diagram showing a relationship between a suction part, a main body part and a blocking part.

FIG. 1 is a diagram showing a configuration of a bodily fluid sampler 100 according to a first embodiment. FIG. 2 is a diagram showing a relationship between a suction part 1, a main body part 2 and a blocking part 3. The bodily fluid sampler 100 is provided with a suction part 1, a main body part 2, a blocking part 3 and a pressure generating part 4. The suction part 1, the main body part 2, the blocking part 3 and the pressure generating part 4 are all formed by, for example, a transparent or translucent resin material.

The suction part 1 includes a suction port 11 and a suction plate 12. The suction port 11 includes therein an accumulation part 13 where the bodily fluid sucked through the suction plate 12 is accumulated. When a user immerses the suction plate 12 in the bodily fluid, being the sampling target, the bodily fluid is sucked into the suction port 11, due to capillarity, and is accumulated in the accumulation part 13.

The suction port 11 has the smallest inner diameter at the part where it is connected to the suction plate 12 and has a tapered form in which the inner diameter thereof increases as the distance from the suction plate 12 increases. The accumulation part 13 also has a tapered form in which the inner diameter thereof increases as the distance from the suction plate 12 increases. Since the accumulation part 13 has such a tapered form, the sucked bodily fluid diffuses within the accumulation part 13 and the bodily fluid can be easily sucked.

The suction plate 12 has a funnel shape with the narrowest part being connected to the suction port 11. The bodily fluid can be efficiently sucked into the suction port 11 due to the fact that the suction plate 12 has a funnel shape.

The main body part 2 includes ventilation channels 21 (a ventilation channel 21a and a ventilation channel 21b) which allow gas for discharging the bodily fluid sucked by the suction part 1 to pass therethrough. In particular, the ventilation channels 21 allow the gas for discharging the bodily fluid to run therethrough toward the suction part 1 by means of the pressure that is generated by the pressure generating part 4 and that moves the gas to the side of the suction part 1. For example, the bodily fluid accumulated in the accumulation part 13 is discharged, via the suction plate 12, by means of the air taken in from the outside and flowing through the ventilation channels 21. The ventilation channel 21a and the ventilation channel 21b are coupled to each other, and the gas runs from the ventilation channel 21a to the ventilation channel 21b by means of the pressure generated by the pressure generating part 4.

In addition, the main body part 2 includes a coupling part 22. The coupling part 22 is a cylindrical section formed so as to be coupled to the suction part 1. The outer diameter of the region of the suction part 1 making contact with the main body part 2 is smaller than the inner diameter of the coupling part 22, and the suction part 1 is provided inside the coupling part 22. More specifically, the suction part 1 and the main body part 2 are connected together in a detachable manner by the fact that, for example, the suction part 1 is inserted into the coupling part 22.

The blocking part 3 is provided between the main body part 2 and the suction part 1. A tapered opening part 31 is provided in the blocking part 3, wherein the inner diameter of the tapered opening part 31 on the side of the main body part 2 is smaller than the inner diameter thereof on the side of the suction part 1. The blocking part 3 prevents the bodily fluid sucked by the suction part 1 from flowing into the main body part 2.

Figure 3A:
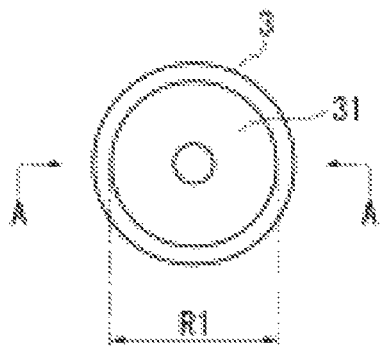
FIG. 3A contains diagrams showing a shape of a blocking part.
Figure 3B:
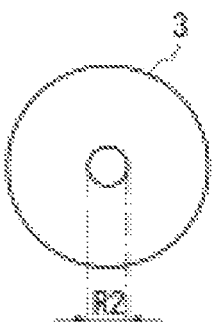
FIG. 3B contains diagrams showing a shape of a blocking part.
Figure 3C:
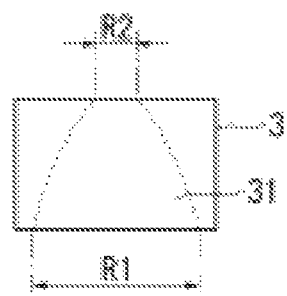
FIG. 3C contains diagrams showing a shape of a blocking part.
Figure 4:
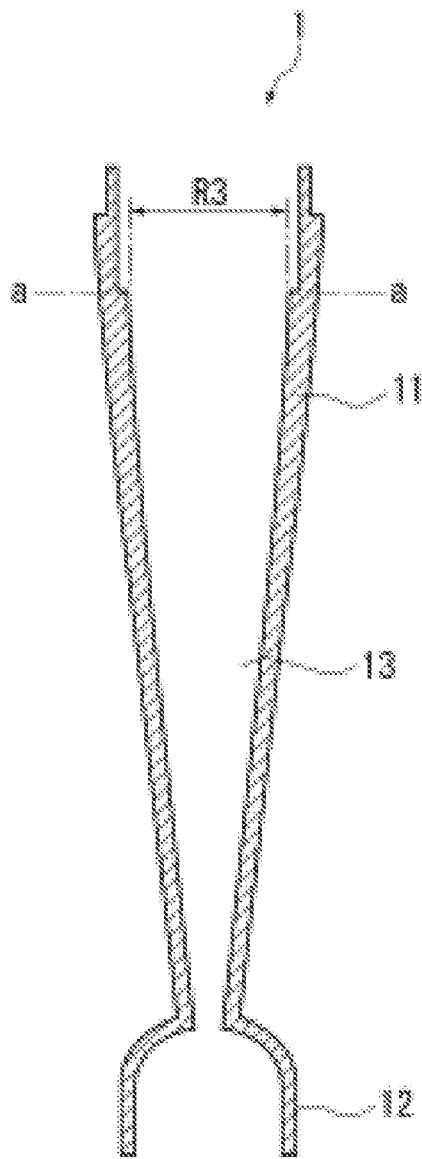
FIG. 4 is a cross-sectional view of a suction part.
Figure 5:
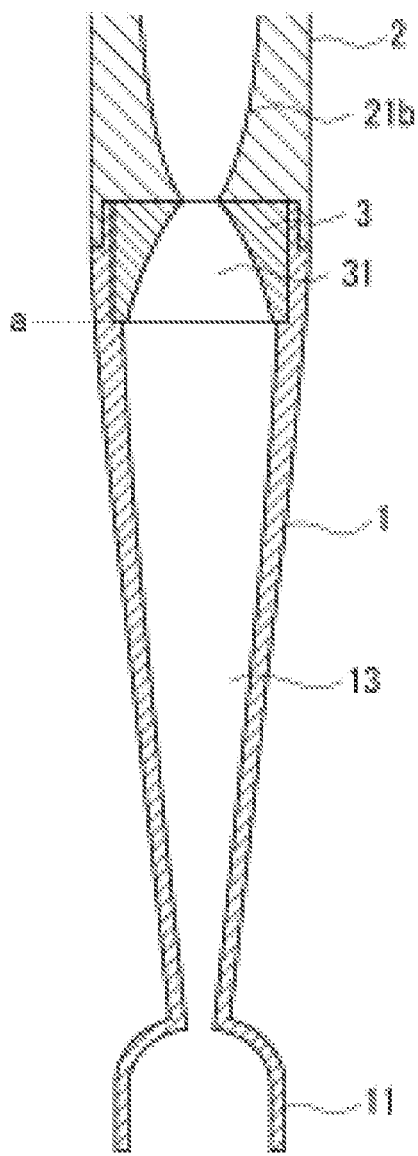
FIG. 5 is a cross-sectional view in the state in which a suction part, a main body part and a blocking part are coupled together.

FIG. 3 contains diagrams showing a shape of the blocking part 3. FIG. 3(a) is a plan view of the blocking part 3 on the side of the suction part 1. FIG. 3(b) is a plan view of the blocking part 3 on the side of the main body part 2. FIG. 3(c) is a cross-sectional view along A-A of the blocking part 3. FIG. 4 is a cross-sectional view of the suction part 1. FIG. 5 is a cross-sectional view in the state in which the suction part 1, the main body part 2 and the blocking part 3 are coupled together. As shown in FIG. 3, the inner diameter of the opening part 31 on the side of the suction part 1 is R1 and the inner diameter on the side of the main body part 2 is R2, and R1>R2.

As shown in FIG. 4, a step is formed on the inner surface of the suction port 11 at a position "a," which is a surface position where the suction part 1 and the surface of the blocking part 3 on the suction part side make contact with each other. The inner diameter of the accumulation part 13 at the position "a" is R3. The outer diameter of the blocking part 3 is smaller than the inner diameter of the suction part 1 at the position where the suction part 1 makes contact with the main body part 2, and the blocking part 3 is provided inside the suction part 1.

As shown in FIG. 5, the blocking part 3 is inserted into the suction part 1 from the side of the main body part 2 to the position "a" where the step is provided. Here, the inner diameter of the opening part 31 formed in the blocking part 3 is smaller than the inner diameter of the suction part 1, at the surface where the suction part 1 and the blocking part 3 make contact with each other. More specifically, the inner diameter R1, on the side of the suction part 1, of the opening part 31 formed in the blocking part 3 is smaller than the inner diameter R3 of the suction part 1 at the position "a." As a result, a step is generated at the position "a" by the fact that blocking part 3 projects inward under the state in which the blocking part 3 is inserted into the suction part 1. The presence of this step prevents the bodily fluid sucked by the suction part 1 from flowing into the main body part 2.

In particular, the bodily fluid, in which the suction plate 12 is immersed, flows into the accumulation part 13 through capillarity. The bodily fluid continues to flow in until it reaches the position "a"; however, the stress generated by the step provided at the position "a" is larger than the pressure for causing the bodily fluid to flow in by the capillarity, and thus, the bodily fluid is prevented from flowing into the side closer to the main body part 2 than the position "a." Accordingly, the user can suck the bodily fluid up to the position "a" by only immersing the tip of the suction part 1 in the bodily fluid.

It should be noted that the size of the step provided at the position "a," namely, the length of R3–R1, can be determined based on the viscosity of the bodily fluid to be sampled.

The bodily fluid that has been sucked up to the position "a" can be discharged by the pressure generated by the pressure generating part 4. The pressure generating part 4 may be configured by, for example, a dropping pipet or a piston, and causes the gas containing an air taken from the outside or the gas remaining in the main body part 2 to flow into the ventilation channel 21a of the main body part 2. The gas which has flowed into ventilation channel 21a pushes out the bodily fluid accumulated in the accumulation part 13 via the ventilation channel 21b and the opening part 31. It should be noted that the pressure generating part 4 includes an opening 41 for releasing the gas contained in the suction part 1 while the suction part 1 sucks the bodily fluid. The bodily fluid contained in the suction part 1 can be discharged by the user covering such opening with his/her fingers.

Now, the ventilation channel 21b has the smallest inner diameter at the surface where the main body part 2 and the blocking part 3 make contact with each other. The ventilation channel 21b has, for example, a tapered form in which the inner diameter thereof decreases as the distance to the blocking part 3 decreases. Since the ventilation channel 21b has such a tapered form, the pressure of the gas that has flowed in from the pressure generating part 4 increases as it approaches the blocking part 3, and thus, the pressure for discharging the bodily fluid also increases.

In addition, the inner diameter of the ventilation channel 21b at the surface where the main body part 2 and the blocking part 3 make contact with each other has a size equal to or larger than the inner diameter of the opening part 31 at the surface where the main body part 2 and the blocking part 3 make contact with each other. Preferably, the inner diameter of the ventilation channel 21b at the surface where the main body part 2 and the blocking part 3 make contact with each other has a size the same as that of the inner diameter of the opening part 31 at the surface where the main body part 2 and the blocking part 3 make contact with each other. The inner diameter of the ventilation channel 21b at the surface where the main body part 2 and the blocking part 3 make contact with each other having the size equal to or larger than the inner diameter of the opening part 31 allows all the gas supplied via the ventilation channel 21b to be used for discharging the bodily fluid.

The gas that has flowed into the opening part 31 is diffused diagonally by the tapered form of the opening part 31, and a pressure is applied to the entire surface of the bodily fluid accumulated in the accumulation part 13. Due to the gas flowing in a diagonal direction, a gas eddy is unlikely to occur, and thus, substantially all the bodily fluid can be discharged without any bodily fluid remaining at the step part at the position "a." The user may encapsulate the discharged bodily fluid into another container and send it off to an inspection organization. It should be noted that, when the size of the step is determined based on the viscosity of the bodily fluid, the bodily fluid is prevented from remaining on the lower side of the step by allowing the step to have the minimum size necessary for preventing the inflow of the bodily fluid by the capillarity.

As described above, the inner diameter R1, on the side of the suction part 1, of the opening part 31 formed in the blocking part 3 is smaller than the inner diameter R3 of the suction part 1 on the side of the blocking part 3, and thus, a step is present at the joining part between the blocking part 3 and the suction part 1 in the bodily fluid sampler. As a result, the inflow of the bodily fluid at the time of sucking the bodily fluid automatically stops at the position of the step, and thus, a precise amount of bodily fluid can be sampled. In addition, due to the fact that the opening part 31 has a tapered form, the sampled bodily fluid can be discharged without any residue. Accordingly, the user can sample a precise amount of bodily fluid and send it off to an inspection organization.

It should be noted that, since the suction part 1 may be connected to the main body part 2, in a detachable manner, with the blocking part 3 being provided to the suction part 1, the amount of the bodily fluid to be sucked can be freely selected by interchangeably using the suction parts 1 which each have different capacities of the accumulation part 13. Accordingly, it is possible to sample an appropriate amount of bodily fluid depending on the types of examination by using the bodily fluid sampler 100 according to the present embodiment.

(Variations)

Figure 6:
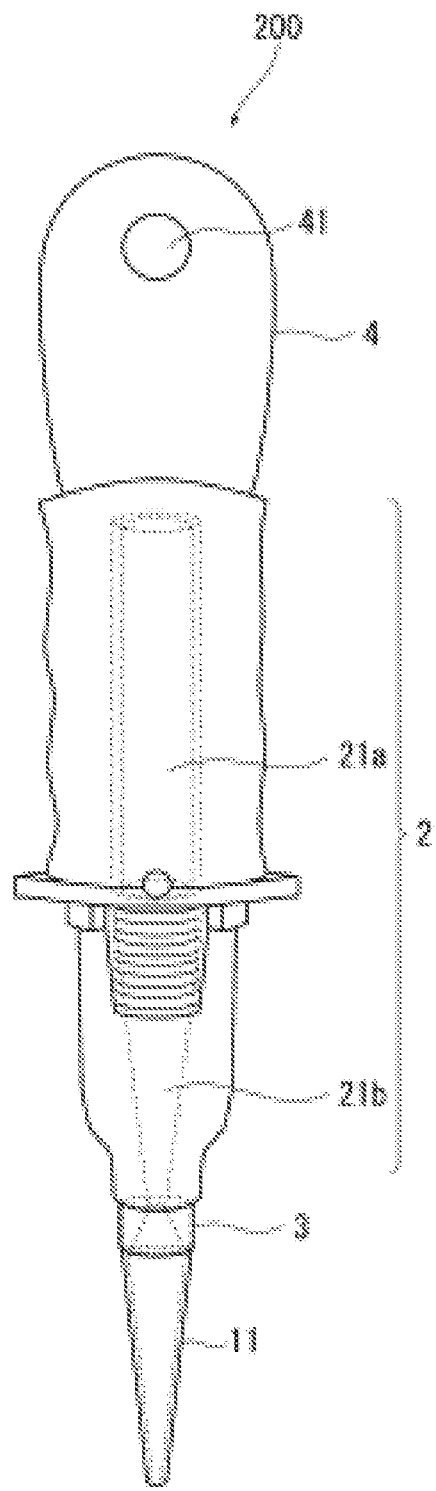
FIG. 6 is a diagram showing a configuration of a bodily fluid sampler according to a variation of the first embodiment.

FIG. 6 is a diagram showing a configuration of a bodily fluid sampler 200 according to a variation of the first embodiment. The bodily fluid sampler 200 differs from the bodily fluid sampler 100 shown in FIG. 1 with respect to the point that it is not provided with a suction plate 12 at the tip thereof; however, the rest is the same. Thus, various variations may be contrived for the embodiments of the bodily fluid sampler according to the present invention, and such variations also fall under the technical scope of the present invention.

(Experimental Examples)

The sampling amounts of the bodily fluid sampler 100 were assayed using a capacity assay method of a quantitative sampling tool based on a solution containing an indicator substance. First, 100 (ml) of the solution containing an indicator substance, in which 1000 (mg) of D(+)-glucose, 1000 (mg) of $NaN_3$, 1000 (mg) of alginate sodium and a tiny amount of brilliant blue are dissolved, was prepared.

Next, by means of the bodily fluid sampler 100, whose sampling amount is 25 (μl), the above-described solution containing an indicator substance was automatically sucked utilizing the capillarity. The suction automatically stopped when the sampling amount reached a predetermined amount.

Subsequently, the sampled solution containing an indicator substance was discharged into saline, which was dispensed in the amount of 500 (μl) in a precise manner by means of an auto-pipette (Eppendorf Reference), and prewashing was carried out five times. After mixing the solution containing an indicator substance which was diluted with saline, the glucose concentration was analyzed using an automatic analysis device (BM 6050 manufactured by JEOL Ltd.). In addition, the glucose concentration of the solution containing an indicator substance prior to dilution was also analyzed.

If the glucose concentration of the solution containing an indicator substance prior to dilution is a (mg/dl), the glucose concentration of the solution containing an indicator substance after dilution is b (mg/dl), and the amount of the solution containing an indicator substance sucked by the bodily fluid sampler 100 is x (μl), the amount of the solution containing an indicator substance sucked by the bodily fluid sampler 100 can be calculated based on: x (μl)=500×b÷(a−b).

Table 1 shows the results of five experiments. The numbers in the table are in units of (μl).

TABLE 1

| No. | Glucose level b | | | $\bar{X}$ | a-b | Calculated amount |
|---|---|---|---|---|---|---|
| 1 | 24.3 | 24.7 | 24.5 | 24.50 | 498.1 | 24.6 |
| 2 | 25.0 | 24.7 | 24.8 | 24.83 | 497.8 | 24.9 |
| 3 | 25.8 | 25.7 | 25.9 | 25.80 | 496.8 | 25.9 |
| 4 | 25.0 | 25.3 | 25.2 | 25.17 | 497.4 | 25.3 |
| 5 | 25.9 | 26.0 | 25.8 | 25.90 | 496.7 | 26.1 |

For glucose concentration analysis, triplicate measurements were carried out, and for calculation of the amount of the solution containing an indicator substance sucked by the bodily fluid sampler 100, an average value of the triplicate measurements was used. The amounts of the solutions containing an indicator substance were, respectively, 523.4 (μl), 521.8 (μl), 521.9 (μl), 523.5 (μl) and 522.2 (μl). For calculation of the amount of the solution containing an indicator substance sucked by the bodily fluid sampler 100, 522.6 (μl), which is an average value of the above amounts, was used.

Based on the result of the experiments, the concordance rate of the calculated sampling amounts was 98.4% to 104.4%, and thus, it was confirmed that the variation in the sampling amounts was sufficiently small.

(Reference Experiment Example)

An experiment for assaying the accuracy of the sampling amounts of an auto-pipette was carried out.

Table 2 shows the results of experiments, similar to the above-described experiments, carried out with an auto-pipette, wherein the sampling amount thereof was set to 20 (μl). When the number of times of pre-washing was set to five or more, the calculated sampling amounts stabilized, the average value of the calculated sampling amounts was 20.00 (μl), and the concordance rate with respect to the set sampling amount was 100%.

TABLE 2

| Number of pre-washing | Glucose level b | | | $\bar{X}$ | a-b | Calculated amount |
|---|---|---|---|---|---|---|
| 0 | 16.7 | 16.6 | 16.6 | 16.63 | 486.74 | 17.08 |
| 1 | 19.4 | 19.3 | 19.2 | 19.30 | 484.07 | 19.94 |
| 2 | 19.1 | 19.3 | 19.2 | 19.20 | 484.17 | 19.83 |
| 3 | 19.0 | 18.7 | 18.9 | 18.87 | 484.50 | 19.47 |
| 4 | 19.1 | 19.0 | 19.1 | 19.07 | 484.30 | 19.69 |
| 5 | 19.4 | 19.2 | 19.4 | 19.33 | 484.04 | 19.97 |
| 6 | 19.4 | 19.3 | 19.4 | 19.36 | 484.01 | 20.00 |
| 7 | 19.4 | 19.5 | 19.4 | 19.43 | 483.94 | 20.07 |
| 8 | 19.4 | 19.6 | 19.3 | 19.43 | 483.94 | 20.07 |
| 9 | 19.4 | 19.3 | 19.4 | 19.37 | 484.00 | 20.01 |
| 10 | 19.2 | 19.2 | 19.4 | 19.37 | 484.10 | 19.90 |

Table 3 shows the results of experiments, similar to the above-described experiments, carried out with an auto-pipette, wherein the sampling amount thereof was set to 50 (μl). Since it was proved, from the results of the experiments in which the sampling amount was set to 20 (μl), that the calculated sampling amounts stabilized when the number of times of pre-washing was set to five or more, the present experiments were carried out with the number of times of pre-washing set to five or more. The average value of the calculated sampling amounts was 49.90 (μl) and the concordance rate with respect to the set sampling amount was 99.8%.

TABLE 3

| Number of pre-washing | Glucose level b | | | $\bar{X}$ | a-b | Calculated amount |
|---|---|---|---|---|---|---|
| 5 | 45.7 | 45.7 | 45.6 | 45.67 | 457.70 | 49.89 |
| 6 | 45.8 | 45.5 | 45.6 | 45.63 | 457.74 | 49.84 |
| 7 | 45.6 | 45.5 | 45.4 | 45.50 | 457.87 | 49.69 |
| 8 | 45.8 | 45.6 | 45.5 | 45.63 | 457.74 | 49.84 |
| 9 | 45.6 | 45.6 | 45.7 | 45.63 | 457.74 | 49.84 |
| 10 | 46.1 | 46.0 | 46.0 | 46.03 | 457.34 | 50.32 |

Table 4 shows the results of experiments, similar to the above-described experiments, carried out with an auto-pipette, wherein the sampling amount thereof was set to 100 (μl). The average value of the calculated sampling amounts was 100.84 (μl) and the concordance rate with respect to the set sampling amount was 100.8%.

TABLE 4

| Number of pre-washing | Glucose level b | | | $\bar{X}$ | a-b | Calculated amount |
|---|---|---|---|---|---|---|
| 5 | 84.6 | 84.6 | 84.7 | 84.63 | 418.74 | 101.05 |
| 6 | 84.8 | 84.2 | 84.4 | 84.47 | 418.90 | 100.82 |
| 7 | 83.8 | 83.8 | 83.8 | 83.80 | 419.57 | 99.86 |
| 8 | 84.5 | 84.3 | 84.5 | 84.43 | 418.94 | 100.77 |
| 9 | 84.5 | 83.8 | 84.1 | 84.13 | 419.24 | 100.34 |
| 10 | 85.0 | 85.0 | 85.3 | 84.10 | 418.27 | 101.73 |

The degree of concordance between the sampling amounts in the case of using the bodily fluid sampler 100 and the set sampling amounts was 98.4% to 104.4%, whereas the degree of concordance between the sampling amounts in the case of using the auto-pipette and the set sampling amounts was 99.8% to 100.8%. It was confirmed that, despite its simple configuration, the bodily fluid sampler 100 is capable of sampling a bodily fluid with a precision comparable to that of an expensive auto-pipette.

<Second Embodiment>

Bodily fluid containers which are capable of accommodating a bodily fluid, such as blood and urine or the like, to be used in examinations for making diagnoses on people's health conditions have been conventionally known (see JP2010-190731A). In such bodily fluid containers, the bodily fluid is prevented from leaking by attaching a lid made of, for example, rubber to the container for accommodating the bodily fluid.

Incidentally, when the bodily fluid to be used in examinations is accommodated in the bodily fluid container, a chemical solution needs to be placed in the bodily fluid container in advance. The chemical solution is for preventing the bodily fluid from being destroyed during the time period between the sampling of the bodily fluid and the examinations thereof. Through recent improvements in bodily fluid sampling methods and examination methods, the trend is to minimize (for example, 2 μl to 20 μl) the sampling amount of bodily fluid to be used in the examinations. Accordingly, the amount of chemical solution to be placed in the bodily fluid container in advance is also in a trend of being minimized.

The chemical solution is accommodated in the bodily fluid container at the time of producing the bodily fluid container. It may take a long time before the bodily fluid container is used after its production, since there are a circulation period and a storage period, and thus, the chemical solution may evaporate and the amount thereof may be reduced. When the amount of the bodily fluid or the chemical solution is small, even a slight amount of reduction in the chemical solution will affect the bodily fluid examinations.

However, in conventional bodily fluid containers, the reduction in the amount of the bodily fluid or the chemical solution was not taken into consideration. Accordingly, there existed a problem to the effect that only reducing the size of a conventional bodily fluid container in accordance with the reduction in the required amount of chemical solution would still cause a reduction in the amount of the chemical solution, due to evaporation, leakage or the like, and thus, the precision of the bodily fluid analysis would decrease.

In order to solve the above problem, an object of a second embodiment is to provide a bodily fluid container and a bodily fluid sampling device, which are capable of preventing, as much as possible, the reduction in the amount of the bodily fluid or the chemical solution.

Figure 7:
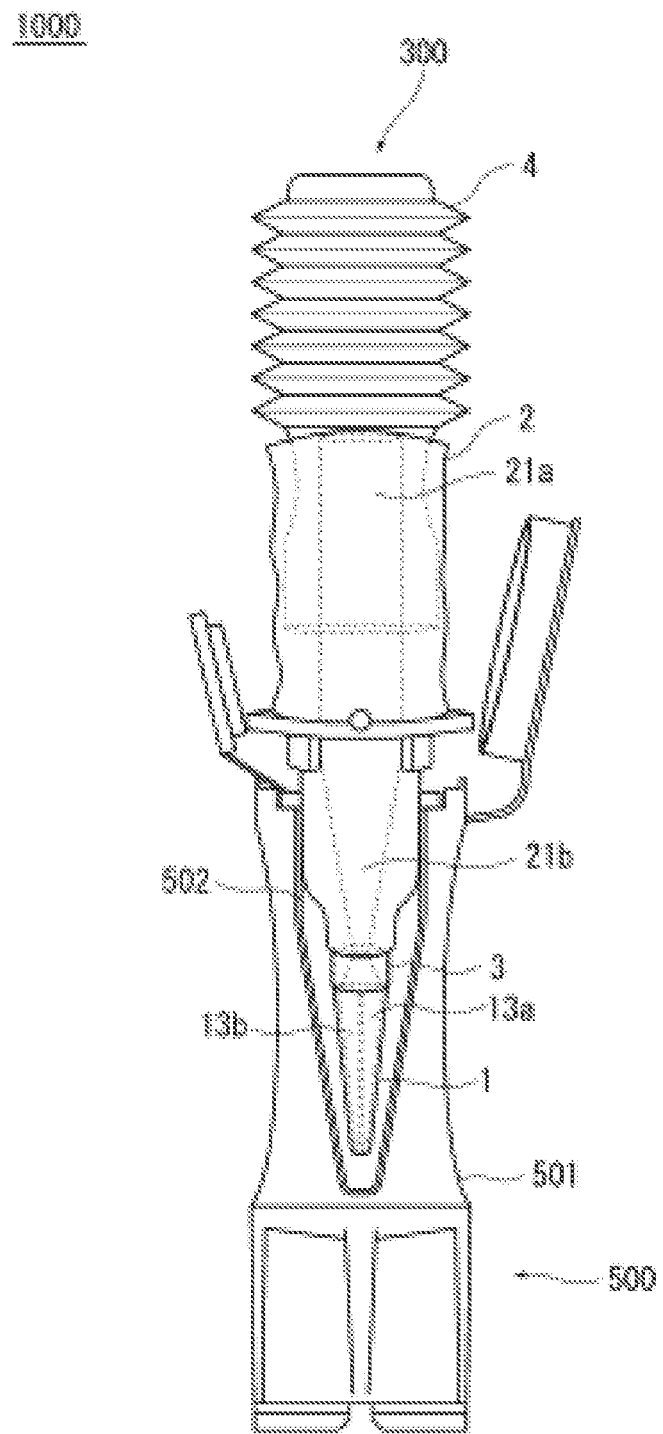
FIG. 7 is a diagram showing a configuration of a bodily fluid sampler according to a second embodiment.

FIG. 7 is a diagram showing a configuration of the bodily fluid sampler 1000 according to the second embodiment. The bodily fluid sampling device 1000 is provided with a bodily fluid sampler 300 and a bodily fluid container 500. The bodily fluid container 500 has a cylindrical shape. FIG. 7 shows an internal state in which the bodily fluid container 500 is inserted onto the bodily fluid sampler 300.

The bodily fluid sampler 300 is provided with a suction part 1, a main body part 2, a blocking part 3 and a pressure generating part 4. The suction part 1, the main body part 2, the blocking part 3 and the pressure generating part 4 are all formed by, for example, a transparent or translucent resin material.

When a user immerses the tip of the suction part 1 in the bodily fluid, being the sampling target, the bodily fluid is sucked into the suction part 1, due to capillarity, and is accumulated in the suction part 1. The suction part 1 includes two cavity parts 13a and 13b, and the bodily fluid is sucked through one of these cavity parts 13a and 13b.

The main body part 2 includes ventilation channels 21 which allow gas for discharging the bodily fluid sucked by the suction part 1 to pass therethrough. In particular, the ventilation channels allow the gas for discharging the bodily fluid to run therethrough toward the suction part 1 by means of the pressure that is generated by the pressure generating part 4 and that moves the gas to the side of the suction part 1. For example, the bodily fluid accumulated in the suction part 1 is discharged, by means of the air taken in from the outside and flowing through the ventilation channels 21 (i.e. ventilation channels 21a and 21b).

The blocking part 3 is provided between the main body part 2 and the suction part 1. A tapered cavity part is formed in the blocking part 3, wherein the inner diameter of the tapered cavity part on the side of the main body part 2 is smaller than the inner diameter thereof on the side of the suction part 1. The blocking part 3 prevents the bodily fluid sucked by the suction part 1 from flowing into the main body part 2.

The bodily fluid container 500 accommodates therein a chemical solution, which is injected in at the time of production, for preventing destruction of a bodily fluid, and a bodily fluid, which is discharged from the bodily fluid sampler 300. In particular, the bodily fluid container 500 is provided with an outer container 501 and an inner container 502, and the chemical solution and the bodily fluid are accommodated in the inner container 502, which is received in the outer container 501. A user can press the pressure generating part 4 in the state in which the bodily fluid sampler 300 is inserted into the bodily fluid container 500, wherein the bodily fluid sampler 300 is in the state in which the bodily fluid is accumulated in the suction part 1, thereby causing the bodily fluid accumulated in the suction part 1 to be accommodated in the inner container 502.

Figure 8:
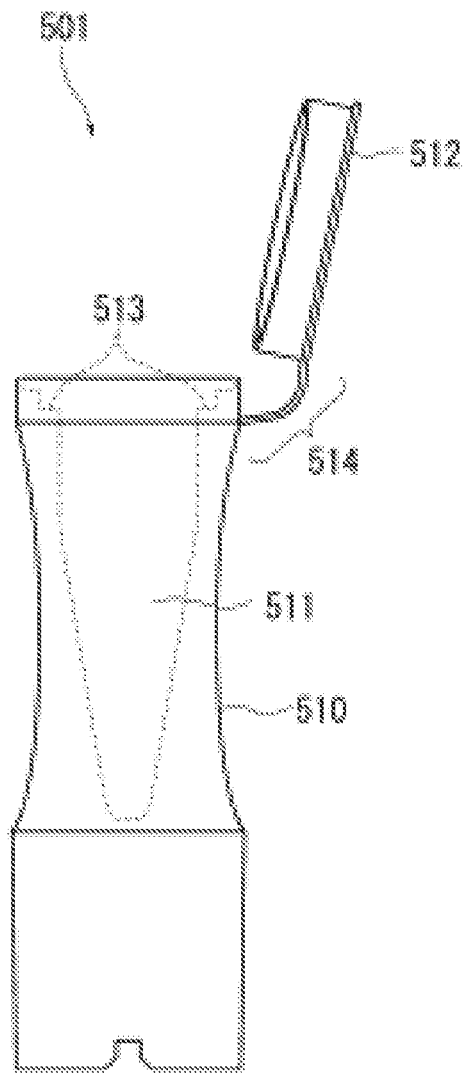
FIG. 8 is a side view of an outer container.

FIG. 8 is a side view of the outer container 501. The outer container 501 includes an outer accommodating part 510, an outer lid part 512 and an outer coupling part 514. The outer accommodating part 510 includes an outer cavity part 511 that receives an inner accommodating part 520 therein. The outer cavity part 511 is a cavity having a shape equivalent to that of the inner container 502 formed inside the outer accommodating part 510.

In addition, the outer accommodating part 510 includes a fixing part 513 that fixes the inner accommodating part 520 to the outer cavity part 511 by the fixing part 513 making contact with a later-described projection part 523 formed on the inner container 502. The fixing part 513 is an annular region formed on the inner wall of the outer accommodating part 510 in a horizontal direction, orthogonal to the direction along which the inner accommodating part 520 is inserted.

The outer lid part 512 closes off the outer cavity part 511 in the state in which the inner accommodating part 520 is inserted in the outer cavity part 511, wherein the inner accommodating part 520 is in the state in which an inner cavity part 521 is closed off by a later-described inner lid part 522. The inner diameter of the outer lid part 512 is larger than the outer diameter of the outer accommodating part 510 at the end part on the opening side of the outer cavity part 511.

The outer coupling part 514 is a member that couples the outer lid part 512 and the outer accommodating part 510 together and that is processed into a shape that can be bent without fracture.

Figure 9:
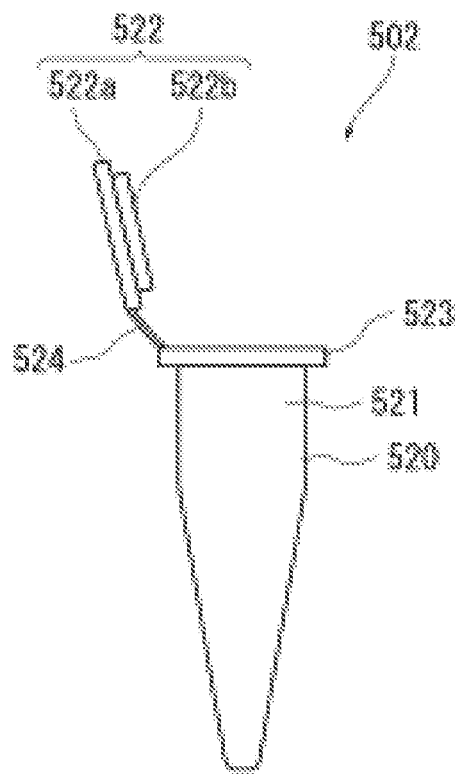
FIG. 9 is a side view of an inner container.

FIG. 9 is a side view of the inner container 502. The inner container 502 includes the inner accommodating part 520, an inner lid part 522 and an inner coupling part 524. The inner accommodating part 520 includes the inner cavity part 521, into which the bodily fluid sampler 300 that samples a bodily fluid can be inserted, and accommodates therein the chemical solution for preventing destruction of the bodily fluid and the bodily fluid sampled by the bodily fluid sampler 300. The inner accommodating part 520 has a shape that allows it to be received in the outer cavity part 511, and also includes the projection part 523 that projects toward the outer accommodating part 510 in the horizontal direction, orthogonal to the direction along which the inner accommodating part 520 is inserted into the outer accommodating part 510.

The inner lid part 522 closes off the inner cavity part 521 of the inner accommodating part 520 in the state in which the bodily fluid sampler 300 is not inserted. The inner lid part 522 includes a first inner lid part 522a, which has a thickness corresponding to the width of the projection part 523, and a second inner lid part 522b, which has a diameter smaller than that of the first inner lid part 522a. Here, the width of the projection part 523 refers to the length of the projection part 523 in the direction along which the inner accommodating part 520 is inserted into the outer accommodating part 510. The thickness of the first inner lid part 522a is a length obtained by subtracting the thickness of the member configuring the projection part 523 from the width of the projection part 523.

Under the state in which the inner lid part 522 closes off the inner cavity part 521, the first inner lid part 522a makes contact with the projection part 523 and the second inner lid part 522b is located, with respect to the projection part 523, on the side of the inner cavity part 521 where the bodily fluid is accommodated. Since the first inner lid part 522a and the second inner lid part 522b have such shapes, under the state in which the inner lid part 522 closes off the inner accommodating part 520, evaporation of the bodily fluid or the chemical solution is easily prevented due to the fact that the path that connects the inner accommodating part 520 to the space outside the inner lid part 522 is lengthened. In addition, even before accommodating the bodily fluid in inner cavity part 521, a reduction in the amount of the chemical solution that has been accommodated in in the bodily fluid container in advance can also be prevented as much as possible.

The inner coupling part 524 is a member that couples the inner lid part 522 and the inner accommodating part 520 together and that is processed into a shape that can be bent without fracture. The inner coupling part 524 is provided with irregularities continuously formed on at least one of the surfaces thereof. The shape of the inner coupling part 524 will be described later in detail.

The inner accommodating part 520, the inner lid part 522 and the inner coupling part 524 are configured by making use of, for example, ABS resin or polycarbonate (PC) as a forming member. By utilizing ABS resin or polycarbonate (PC), which is less subject to liquid absorption, the bodily fluid can be prevented from being absorbed into the inner accommodating part 520 or the inner lid part 522, when it is received in the inner accommodating part 520. It should be noted that other materials, such as polypropylene (PP) or the like, may also be used as a forming member of the inner accommodating part 520, the inner lid part 522 and the inner coupling part 524, depending on the application, such as the case where the chemical solution is to be stored only for a short period of time (for example, approximately one month).

Figure 10:
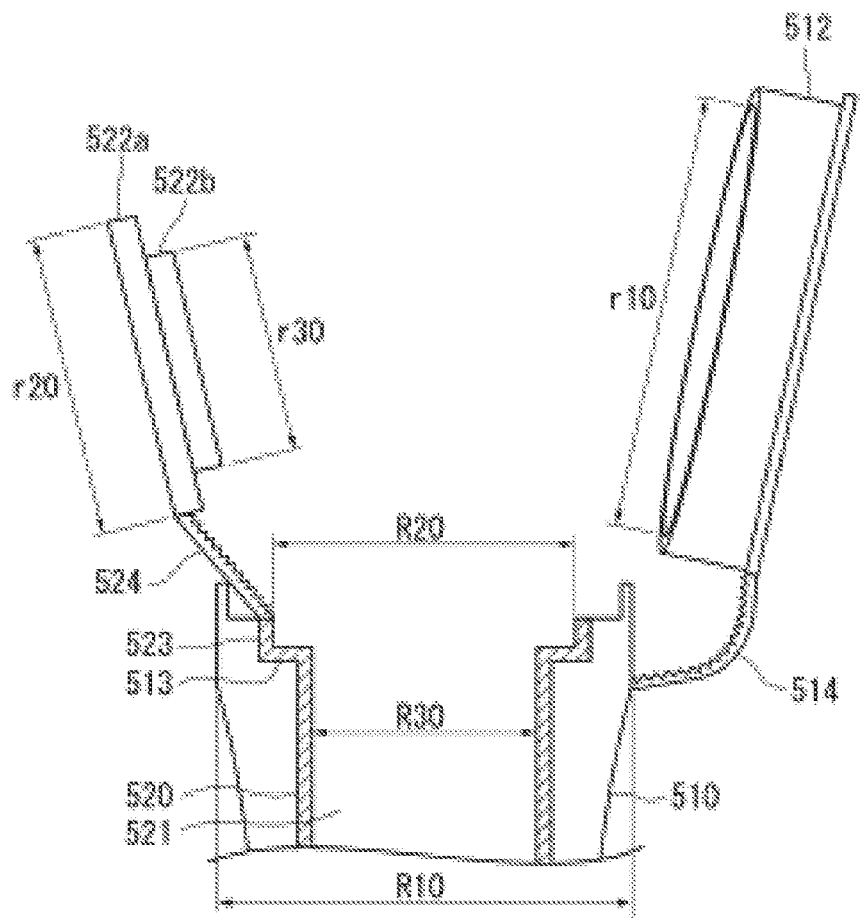
FIG. 10 is an enlarged view of the vicinities of an outer lid part and an inner lid part.

FIG. 10 is an enlarged view of the vicinities of the outer lid part 512 and the inner lid part 522. FIG. 10 shows a side view of the outer lid part 512, the outer coupling part 514, the inner lid part 522 and the inner coupling part 524, and a cross-sectional view of the outer accommodating part 510 and the inner accommodating part 520 in the state in which the inner accommodating part 520 is inserted.

As shown in FIG. 10, if the outer diameter of the outer accommodating part 510 at the end part thereof is R10, the inner diameter of the inner accommodating part 520 at the projection part 523 is R20, the inner diameter of the inner accommodating part 520 at a part below the projection part 523 is R30, the inner diameter of the outer lid part 512 is r10, the diameter of the first inner lid part 522a is r20 and the diameter of the second inner lid part 522b is r30, the relationships, R10<r10, R20>r20 and R30 >r30 , are established. Satisfaction of such relationships allows the inner lid part 522 to close off the inner cavity part 521, and allows the outer lid part 512 to close off the inner cavity part 521, such that it seals the outer accommodating part 510 and covers the inner lid part 522, while the inner lid part 522 seals the inner cavity part 521. More specifically, the bodily fluid container 500 has a double sealing configuration.

Figure 11:
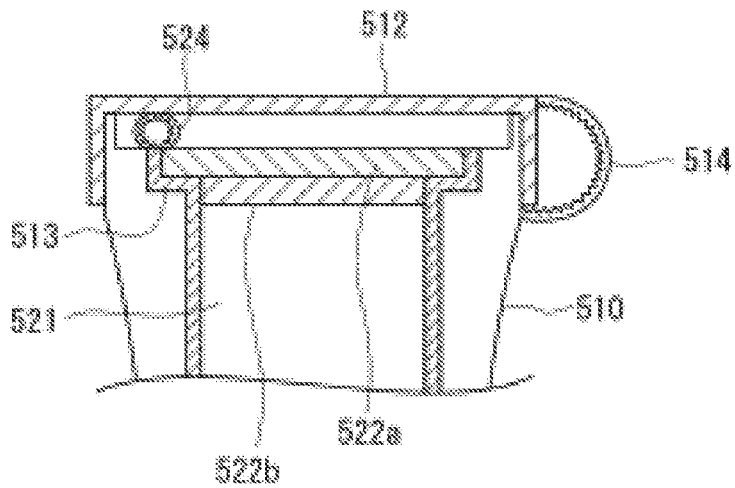
FIG. 11 is a cross-sectional view of the vicinities of the outer lid part and the inner lid part.

FIG. 11 is a cross-sectional view of the vicinities of the outer lid part 512 and the inner lid part 522 in the state in which the outer lid part 512 and the inner lid part 522 are closed. It can be seen that the inner accommodating part 520 is sealed by the fact that the inner lid part 522 is received on the inner side of the projection part 523 which is formed on the inner accommodating part 520. In addition, it can also be seen that a high sealing property is achieved, since the outer lid part 512 covers the inner lid part 522 in the state in which the outer lid part 512 is closely attached to the outer accommodating part 510.

It can also be seen that the inner coupling part 524 is received in the space formed between the inner lid part 522, the outer lid part 512, and the inner wall of the outer accommodating part 510. Since the inner coupling part 524 is formed in a bendable manner, it can be received in the small space formed between the inner lid part 522, the outer lid part 512, and the inner wall of the outer accommodating part 510. It should be noted that, as shown in FIG. 11, the inner wall of the outer accommodating part 510 is preferably formed with steps at the upper part of the fixing part 513, such that the bent inner coupling part 524 can be received.

Figure 12A:
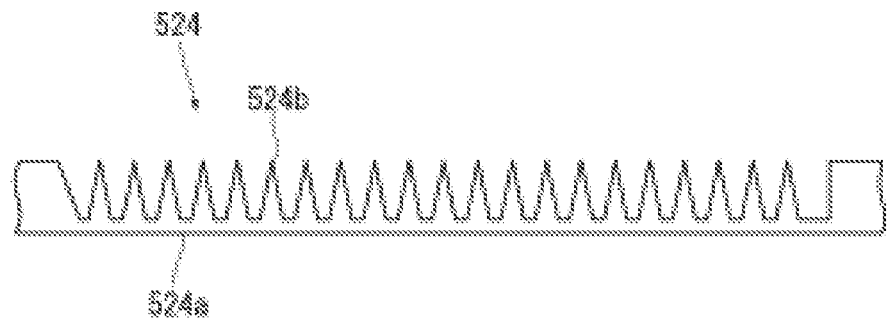
FIG. 12A contains cross-sectional views of an inner coupling part.
Figure 12B:
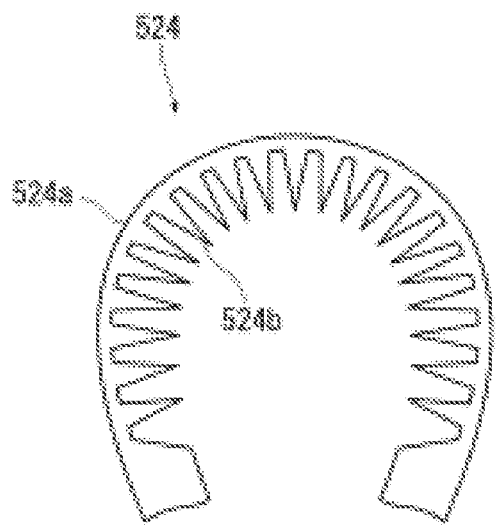
FIG. 12B contains cross-sectional views of an inner coupling part.

FIG. 12 contains cross-sectional views of the inner coupling part 524. The outer coupling part 514 may have a cross section equivalent to that of the inner coupling part 524. FIG. 12(a) shows the inner coupling part 524 in an extended state. FIG. 12(b) shows the inner coupling part 524 in a bent state.

As shown in FIG. 12(a), the inner coupling part 524 includes a base part 524a and a plurality of triangular protrusion parts 524b formed over the base part 524a. The base part 524a can be bent at a curvature larger than the curvature in the state in which the inner lid part 522 is attached to the inner accommodating part 520.

As shown in FIG. 12(b), when the inner coupling part 524 is bent, the base part 524a also bends and the respective orientations of the plurality of the protrusion parts 524b change. More specifically, the plurality of the protrusion parts 524b assumes the state in which each faces toward a predetermined position on the inner side of the bent inner coupling part 524. Since the inner coupling part 524 has such shape, the inner coupling part 524 can be bent, with a large curvature, so as to be received in the small space formed between the inner lid part 522, the outer lid part 512, and the inner wall of the outer accommodating part 510, and it also has a sufficient strength, by making use of ABS resin or polycarbonate which is easily fractured.

Figure 13:
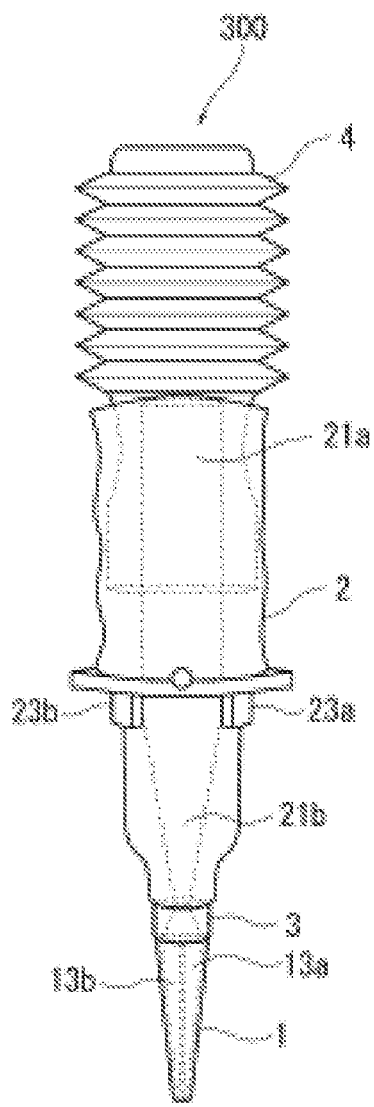
FIG. 13 is a diagram showing a shape of a bodily fluid sampler.

FIG. 13 is a diagram showing a shape of the bodily fluid sampler 300. The bodily fluid sampler 300 includes positioning parts 23 (23a and 23b), which are provided in a boundary region between a region of the main body part 2 to be inserted into the inner accommodating part 520 and a region thereof not to be inserted into the inner accommodating part 520. Although FIG. 13 shows two positioning parts 23, such as a positioning part 23a and a positioning part 23b, the main body part 2 may include any number of positioning parts 23.

In the state in which the bodily fluid sampler 300 is inserted into the inner accommodating part 520, the positioning parts 23 determine the position of the bodily fluid sampler 300 by making contact with at least one of the inner accommodating part 520 and the outer accommodating part 510. For example, when the tips of the positioning parts 23 bump against the projection part 523 by moving the bodily fluid sampler 300 in the direction along which the bodily fluid sampler 300 is inserted into the inner accommodating part 520, the bodily fluid sampler 300 cannot move any further. In the state in which the bodily fluid sampler 300 is inserted into the inner accommodating part 520 up to a position where the positioning parts 23 make contact with at least one of the inner accommodating part 520 and the outer accommodating part 510, the distance between the tip of the bodily fluid sampler 300 and the tip of the inner cavity part 521 of the inner accommodating part 520 is larger than a predetermined value.

For example, at the position where the tips of the positioning parts 23 make contact with the projection part 523, the tip of the bodily fluid sampler 300 is located at a position where it does not make contact with the bodily fluid, which is in the capacity that can be sucked by the suction part 1, or the chemical solution accommodated in the inner accommodating part 520, with such bodily fluid being accommodated in the inner accommodating part 520. In this way, the tip of the bodily fluid sampler 300 is prevented from making contact with the bodily fluid and the chemical solution. Accordingly, the bodily fluid and the chemical solution accommodated in the inner accommodating part 520 are prevented from being reduced in amount due to adhesion of such chemical solution and bodily fluid to the tip of the bodily fluid sampler 300.

The length of the positioning parts 23 is determined based on the length of the suction part 1 and the amount it can suck. The longer the suction part 1 is, the longer the length of the positioning parts 23 is made, and the larger the amount of bodily fluid that can be sucked by the suction part 1 is, the longer the length of the positioning parts 23 is made, and thus, the tip of the bodily fluid sampler 300 is prevented from making contact with the bodily fluid even when the suction part 1 is long and even when the amount that can be sucked is large.

The positioning parts 23 are attached to the main body part 2 in a detachable manner. For example, the positioning part 23 has a convex part which is fixed to the main body part 2 by being inserted into a concave part formed in the main body part 2. Since the positioning part 23 is detachable from the main body part 2, it may be switched with a positioning part 23 having an optimum length depending on the length of the suction part 1 and the amount that can be sucked by the suction part 1. Accordingly, when the suction part 1 is interchangeable in the bodily fluid sampler 300, the positioning part 23 can also be interchanged depending on the interchange of the suction part 1, and thus, the user can use one and the same bodily fluid container 500, even with bodily fluid samplers 300 having different amounts that can be sucked, while switching the amount that can be sucked of the bodily fluid sampler 300.

(Variation 1)

In the above-described embodiment, an example has been described in which the outer accommodating part 510 and the outer lid part 512 are coupled together by means of the outer coupling part 514, and the inner accommodating part 520 and the inner lid part 522 are coupled together by means of the inner coupling part 524. However, the outer accommodating part 510 and the outer lid part 512 may not need to be coupled together, and the inner accommodating part 520 and the inner lid part 522 may also not need to be coupled together.

(Variation 2)

In the above-described embodiment, it has been described that the projection part 523 has an annular shape; however, the projection part 523 may have other shapes. For example, the projection part 523 may be configured by four protrusion parts formed at the end part of the inner accommodating part 520 at 90 degree-intervals, and the inner container 502 may be configured such that it is fixed to the outer container 501 by such protrusion parts making contact with the fixing part 513.

(Variation 3)

In the above-described embodiment, the bodily fluid sampler 300 is capable of making the distance between the tip of the bodily fluid sampler 300 and the tip part of the inner cavity part 521 of the inner accommodating part 520 larger than a predetermined value by the positioning part 23 provided at the main body part 2 making contact with at least one of the inner accommodating part 520 and the outer accommodating part 510. By contrast, the bodily fluid sampler 300 may be configured such that the distance between the tip of the bodily fluid sampler 300 and the tip of the inner cavity part 521 is larger than the predetermined value in the state in which the bodily fluid sampler 300 is inserted into the inner accommodating part 520 up to a position where the bodily fluid sampler 300 has a diameter larger than the inner diameter of the inner cavity part 521. More specifically, by the fact that the main body part 2 has a shape that tapers down as the distance to the tip thereof decreases, the bodily fluid sampler 300 is prevented from being inserted beyond the predetermined position in the inner accommodating part 520, and thus, the suction part 1 can be prevented from making contact with the bodily fluid accommodated in the inner accommodating part 520.

(Variation 4)

In the above-described embodiment, a configuration has been described in which the plurality of protrusion parts 524b are formed on one side of the base part 524a of the inner coupling part 524; however, the inner coupling part 524 may have a rectangular parallelepiped shape without the plurality of the protrusion parts 524b. In addition, as shown in FIG. 14, protrusion parts 524b and protrusion parts 524c may be formed on both sides of the base part 524a.

Figure 14:
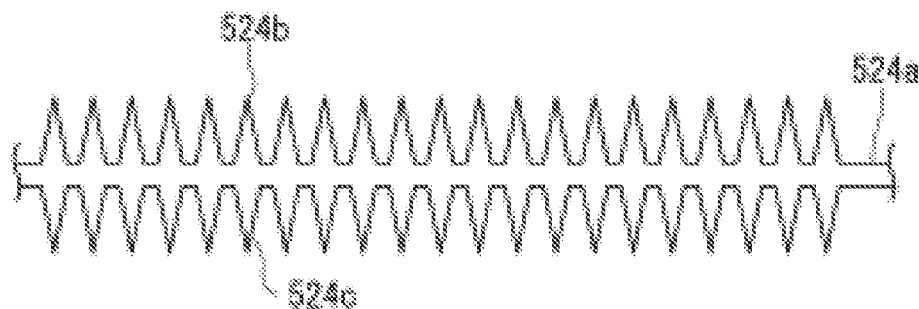
FIG. 14 is a cross-sectional view (a variation) of the inner coupling part.

Moreover, in FIGS. 12 and 14, examples have been described in which the protrusion parts 524b or protrusion parts 524c have a triangular shape; however, they may have other shapes, as long as the width at the tip is smaller than the width at the base.

<Third Embodiment>

A bodily fluid, such as blood and urine or the like, to be used in examinations for making diagnoses on people' health conditions is conventionally accommodated in a bodily fluid container after being sampled by a bodily fluid sampler. JP09-141135A discloses a technique in which the blood accommodated in a tubular body, being the bodily fluid container, is subjected to centrifugal separation to be separated into blood cells and blood plasma, which are constituents of the blood, and in which the blood cell part and the blood plasma part are thereafter taken out. Examinations and analysis on such taken-out blood cell part and blood plasma part allow for diagnoses to be made on people's health conditions.

Incidentally, through improvements in bodily fluid sampling methods and examination methods, the trend is to minimize the sampling amount of bodily fluid to be used in the examinations. In such case, in order to prevent a decrease in examination precision, a bodily fluid container needs to be configured such that a desired component (for example, a blood cell, etc.), being the examination target, can be appropriately taken out from a small amount of sampled bodily fluid. To take out the desired component, it is conceivable to place the bodily fluid container having the bodily fluid accommodated therein into a centrifuge and to carry out centrifugal separation on a component basis. However, when centrifugal separation is carried out using a conventional bodily fluid container, it is necessary to insert a micropipette into the bodily fluid container, in which a plurality of constituents are stacked after the centrifugal separation, and to take out the desired component. This generates a problem to the effect that the desired component and other constituents are mixed.

It should be noted that a thin projecting part which is capable of accommodating part of blood cells of the blood after centrifugal separation is integrally molded at the tip of the tubular body described in JP09-141135A. Such molding is typically implemented using a mold; however, stress concentration is likely to occur at the location where the thin projecting part is molded, during molding using a mold, and therefore, integrally molding the projecting part is difficult.

In order to solve the above problem, an object of a third embodiment is to provide a bodily fluid container, by means of which a desired component within the centrifugally separated bodily fluid can be appropriately taken out.

(Summary of Bodily Fluid Sampling Device)

A summary of a bodily fluid sampling device according to the third embodiment of the present invention will be described with reference to FIGS. 15 and 16.

Figure 15:
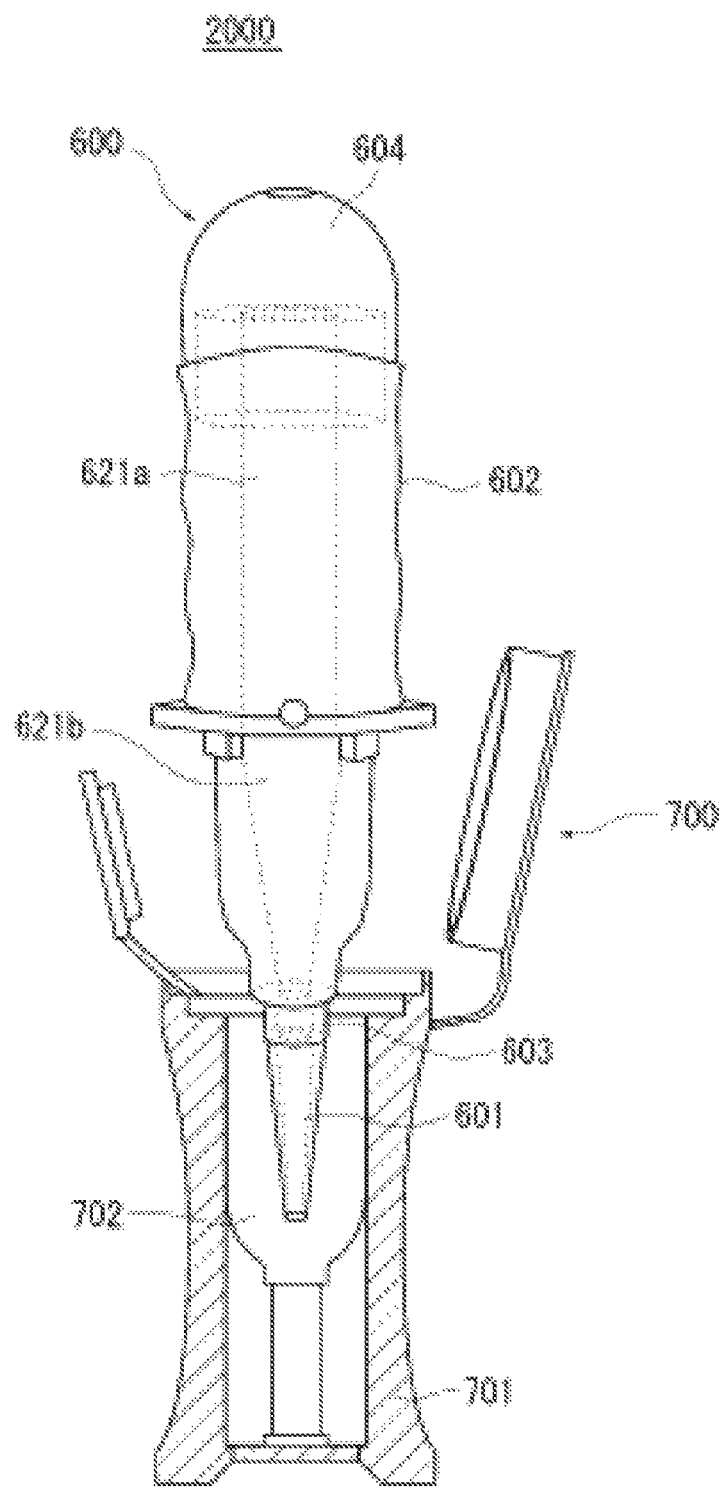
FIG. 15 is a diagram showing a configuration of a bodily fluid sampling device 2000 according to a third embodiment of the present invention.
Figure 16:
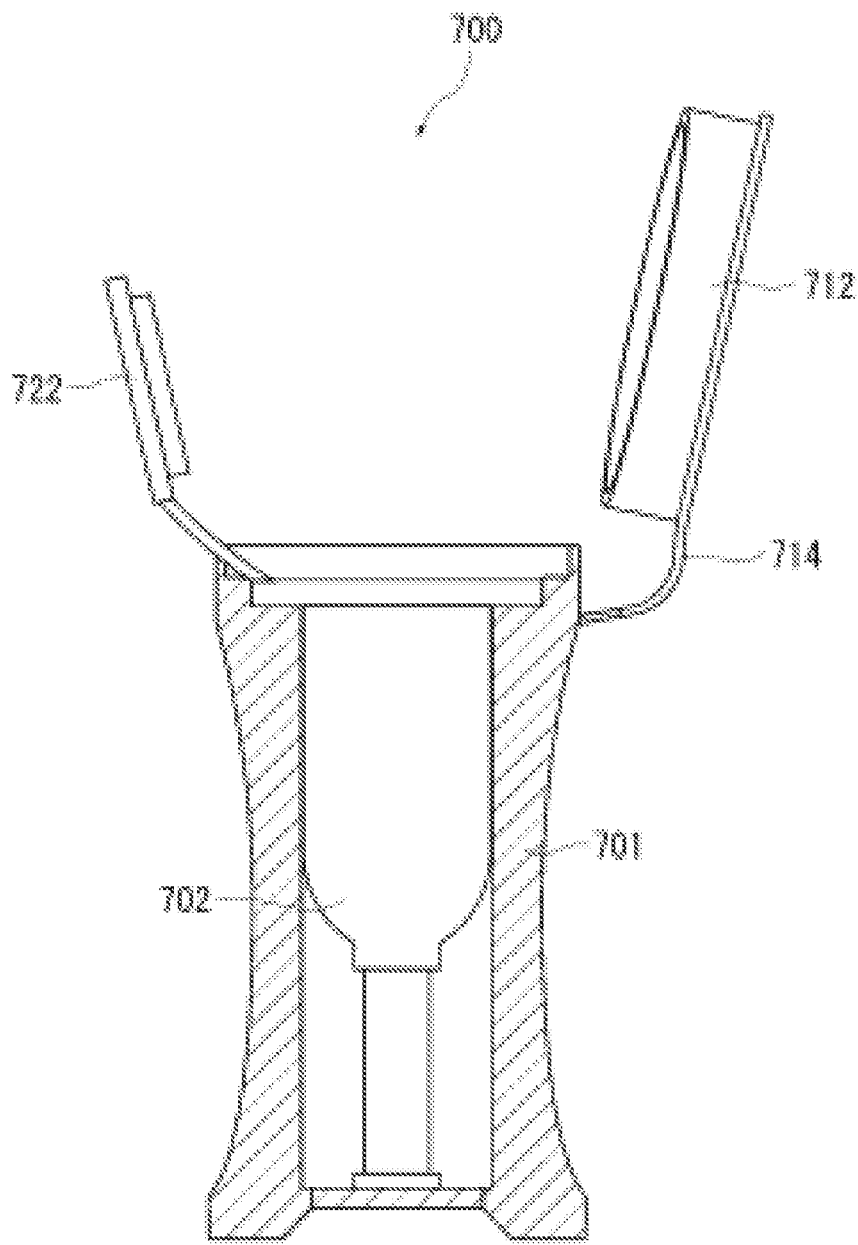
FIG. 16 is a diagram showing a configuration of a bodily fluid container 700 according to the third embodiment.

FIG. 15 is a diagram showing a configuration of the bodily fluid sampling device 2000 according to the third embodiment. FIG. 16 is a diagram showing a configuration of a bodily fluid container 700 according to the third embodiment. The bodily fluid sampling device 2000 is provided with a bodily fluid sampler 600 and the bodily fluid container 700. The bodily fluid container 700 has a cylindrical shape. FIG. 15 shows an internal state in which the bodily fluid container 700 is inserted onto the bodily fluid sampler 600.

The bodily fluid sampler 600 is provided with a suction part 601, a main body part 602, a blocking part 603 and a pressure generating part 604. The suction part 601, the main body part 602, the blocking part 603 and the pressure generating part 604 are all formed by, for example, a transparent or translucent resin material.

When a user immerses the tip of the suction part 601 in the bodily fluid, being the sampling target, the bodily fluid is sucked into the suction part 601, due to capillarity, and is accumulated in the suction part 601. The suction part 601 includes two cavity part 613a and 613b, and the bodily fluid is sucked through one of these cavity parts 613a and 613b.

The main body part 602 includes ventilation channels which allow gas for discharging the bodily fluid sucked by the suction part 601 to pass therethrough. In particular, the ventilation channels allow the gas for discharging the bodily fluid to run therethrough toward the suction part 601 by means of the pressure that is generated by the pressure generating part 604 and that moves the gas to the side of the suction part 601. For example, the bodily fluid accumulated in the suction part 601 is discharged, by means of the air taken in from the outside and flowing through the ventilation channels 621 (i.e. ventilation channels 621a and 621b).

The blocking part 603 is provided between the main body part 602 and the suction part 601. A tapered cavity part is formed in the blocking part 603, wherein the inner diameter of the tapered cavity part on the side of the main body part 602 is smaller than the inner diameter thereof on the side of the suction part 601. The blocking part 603 prevents the bodily fluid sucked by the suction part 601 from flowing into the main body part 602.

It should be noted that the suction part 601 and the blocking part 603 are capable of being attached in a detachable manner. In such case, the suction part and the blocking part having a size depending on the amount of blood to be sampled may be selected and attached.

The bodily fluid container 700 accommodates therein a chemical solution, which is injected in at the time of production, for preventing destruction of a bodily fluid, and a bodily fluid, which is discharged from the bodily fluid sampler 600. In particular, as shown in FIG. 16, the bodily fluid container 700 is provided with an outer container 701 and an inner container 702, and the chemical solution and the bodily fluid are accommodated in the inner container 702, which is received in the outer container 701. A user presses the pressure generating part 604 in the state in which the bodily fluid sampler 600 is inserted into the bodily fluid container 700, wherein the bodily fluid sampler 600 is in the state in which the bodily fluid is accumulated in the suction part 601, thereby causing the bodily fluid accumulated in the suction part 601 to be received in the inner container 702.

(Configuration of Bodily Fluid Container 700)

The detailed configuration of the bodily fluid container 700 will be described with reference to FIGS. 17 and 18. Hereinafter, the description on the configuration of the outer container 701 configuring the bodily fluid container 700 will be followed by the description of the configuration of the inner container 702.

(Outer Container 701)

Figure 17:
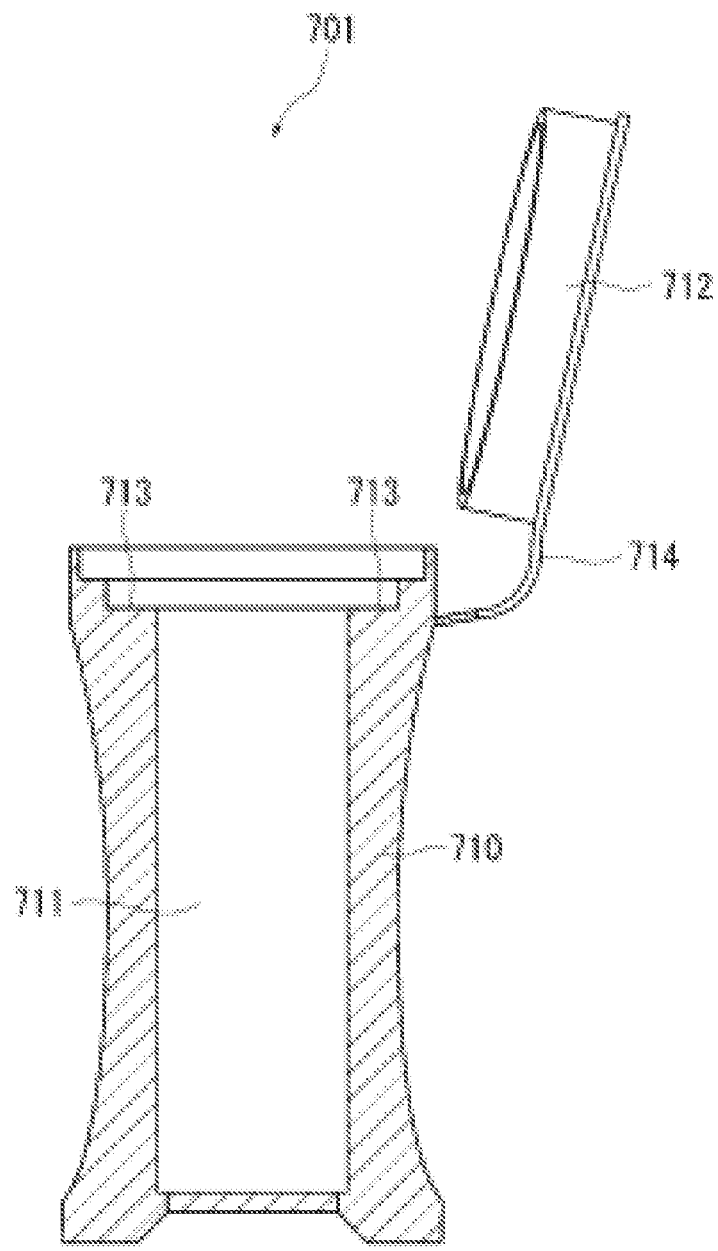
FIG. 17 is a side view of an outer container 701 according to the third embodiment.

FIG. 17 is a side view of the outer container 701 according to the third embodiment. The outer container 701 receives the inner container 702. The outer container 701 includes an outer accommodating part 710, an outer lid part 712 and an outer coupling part 714.

The outer accommodating part 710 includes an outer cavity part 711 that receives the inner container 702 therein. The outer cavity part 711 is formed inside the outer accommodating part 710 and is a cavity slightly larger than the inner container 702.

In addition, the outer accommodating part 710 includes a fixing part 713 that fixes the inner container 702 to the outer cavity part 711 by the fixing part 713 making contact with a later-described projection part 723 formed on the inner container 702. The fixing part 713 is an annular region formed on the inner wall of the outer accommodating part 710 in a horizontal direction, orthogonal to the direction along which the inner container 702 is inserted.

Figure 19:
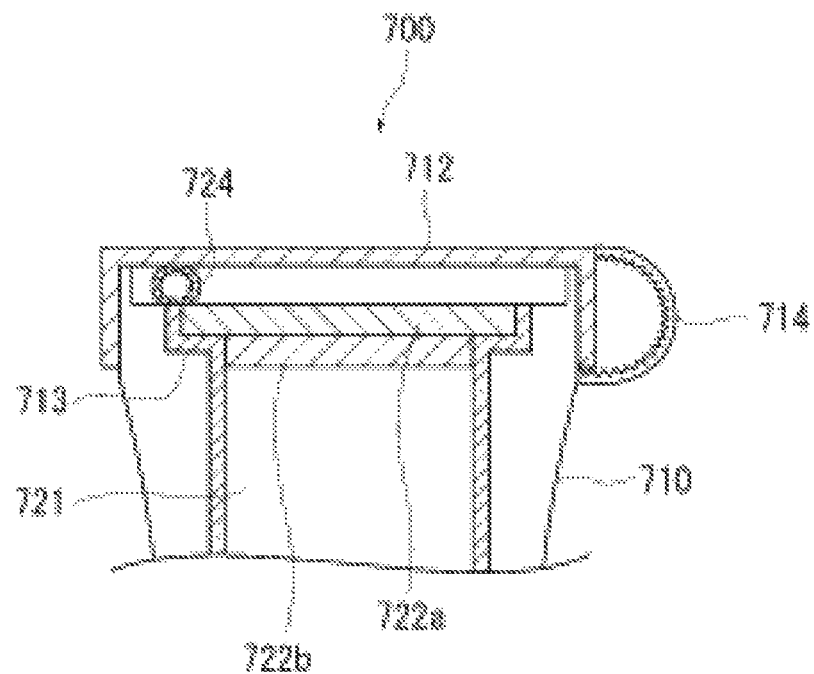
FIG. 19 is a cross-sectional view of the vicinities of an outer lid part 712 and an upper lid part 722 in the state in which the outer lid part 712 and the upper lid part 722 are closed.

The outer lid part 712 closes off the outer cavity part 711 in the state in which the inner container 702 is inserted in the outer cavity part 711, wherein the inner container 702 is in the state in which a first cavity part 721 is closed off by a later-described upper lid part 722 of the inner container 702 (see FIG. 19). More specifically, a double sealing configuration is provided. The inner diameter of the upper lid part 712 is larger than the outer diameter of the outer accommodating part 710 at the end part on the opening side of the outer cavity part 711. It should be noted that FIG. 19 is a cross-sectional view of the vicinities of the outer lid part 712 and the upper lid part 722 in the state in which the outer lid part 712 and the upper lid part 722 are closed.

The outer coupling part 714 is a member that couples the outer lid part 712 and the outer accommodating part 710 together and that is processed into a shape that can be bent without fracture.

(Inner Container 702)

Figure 18:
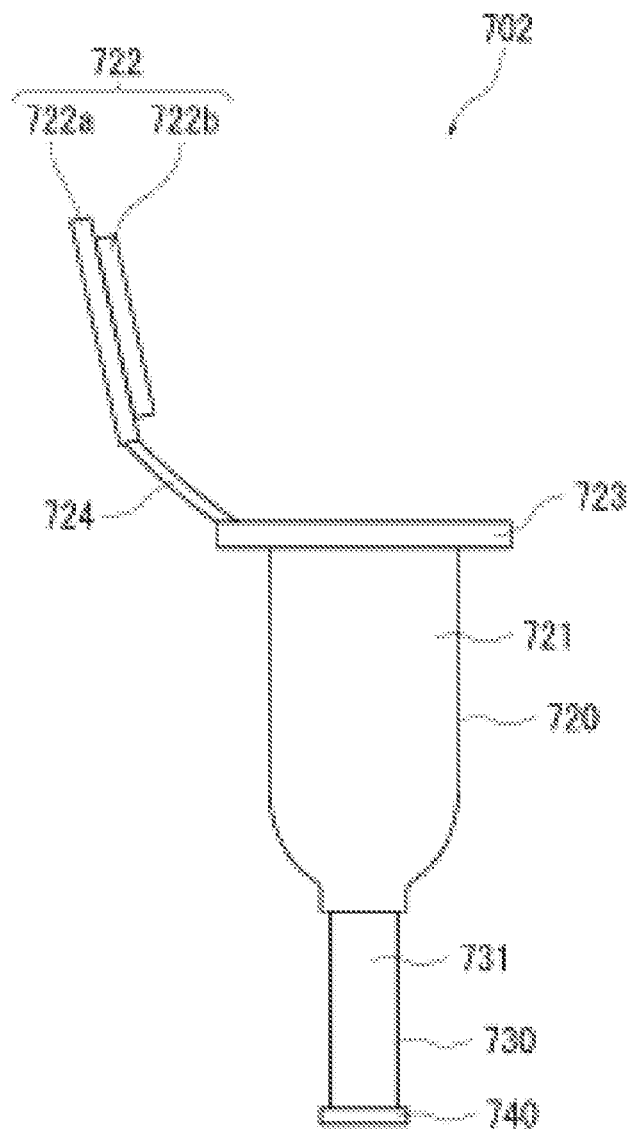
FIG. 18 is a side view of an inner container 702 according to the third embodiment.

FIG. 18 is a side view of the inner container 702 according to the third embodiment. The inner container 702 accommodates therein a bodily fluid subject to centrifugal separation. The inner container 702 includes a first accommodating part 720, an upper lid part 722, an inner coupling part 724, a second accommodating part 730 and a lower lid part 740. It should be noted that the description will be given hereinafter using blood containing blood cells and blood plasma as an example of the bodily fluid.

The first accommodating part 720 includes a first cavity part 721, into which the bodily fluid sampler 600 for sampling blood is insertable, and accommodates therein a chemical solution for preventing destruction of a blood and blood sampled by the bodily fluid sampler 600. The first accommodating part 720 has a shape that allows it to be received in the outer cavity part 711, and also includes the projection part 723 that projects toward the outer accommodating part 710 in the horizontal direction, orthogonal to the direction along which the first accommodating part 720 is inserted into the outer accommodating part 710.

The upper lid part 722 closes off the first cavity part 721 of the first accommodating part 720 in the state in which the bodily fluid sampler 600 is not inserted. The upper lid part 722 includes a first upper lid part 722a having a thickness corresponding to the width of the projection part 723 and a second upper lid part 722b having a diameter smaller than that of the first upper lid part 722a.

Under the state in which the upper lid part 722 closes off the first cavity part 721, the first upper lid part 722a makes contact with the projection part 723 and the second upper lid part 722b is located, with respect to the projection part 723, on the side of the first cavity part 721 where the blood is accommodated. Since the first upper lid part 722a and the second upper lid part 722b have such shapes, under the state in which the upper lid part 722 closes off the first accommodating part 720, evaporation of the blood or the chemical solution is easily prevented due to the fact that the path that connects the first accommodating part 720 to the space outside the upper lid part 722 is lengthened. In addition, even before accommodating the blood in the first cavity part 721, a reduction in the amount of the chemical solution that has been accommodated in the bodily fluid container in advance can also be prevented as much as possible.

The inner coupling part 724 is a member that couples the upper lid part 722 and the first accommodating part 720 together and that is processed into a shape that can be bent without fracture. The inner coupling part 724 is provided with irregularities continuously formed on at least one of the surfaces thereof (see FIG. 19).

The first accommodating part 720, the upper lid part 722 and the inner coupling part 724 are configured by making use of, for example, ABS resin or polycarbonate (PC) as a forming member. By utilizing ABS resin or polycarbonate (PC), which is less subject to liquid absorption, the blood can be prevented from being absorbed into the first accommodating part 720 or the upper lid part 722, when it is received in the first accommodating part 720. It should be noted that other materials, such as polypropylene (PP) or the like, may also be used as a forming member of the first accommodating part 720, the upper lid part 722 and the inner coupling part 724, depending on the application, such as the case where the chemical solution is to be stored only for a short period of time (for example, approximately one month).

The second accommodating part 730 includes a second cavity part 731 that receives therein blood together with the first cavity part 721. The second accommodating part 730 is formed in a cylindrical shape, and the inner diameter of the second cavity part 731 is smaller than the inner diameter of the first cavity part 721. The second cavity part 731 provides a function by which blood containing both blood cells and blood plasma is accommodated therein prior to centrifugal separation; however, only the blood cells among the blood cells and the blood plasma are accommodated therein after centrifugal separation. The length of the second cavity part 731 in the axial direction is set such that the second cavity part 731 accommodates therein the blood cells after centrifugal separation. It should be noted that the second cavity part 731 may accommodate a small amount of blood plasma on the upper side thereof.

Figure 20:
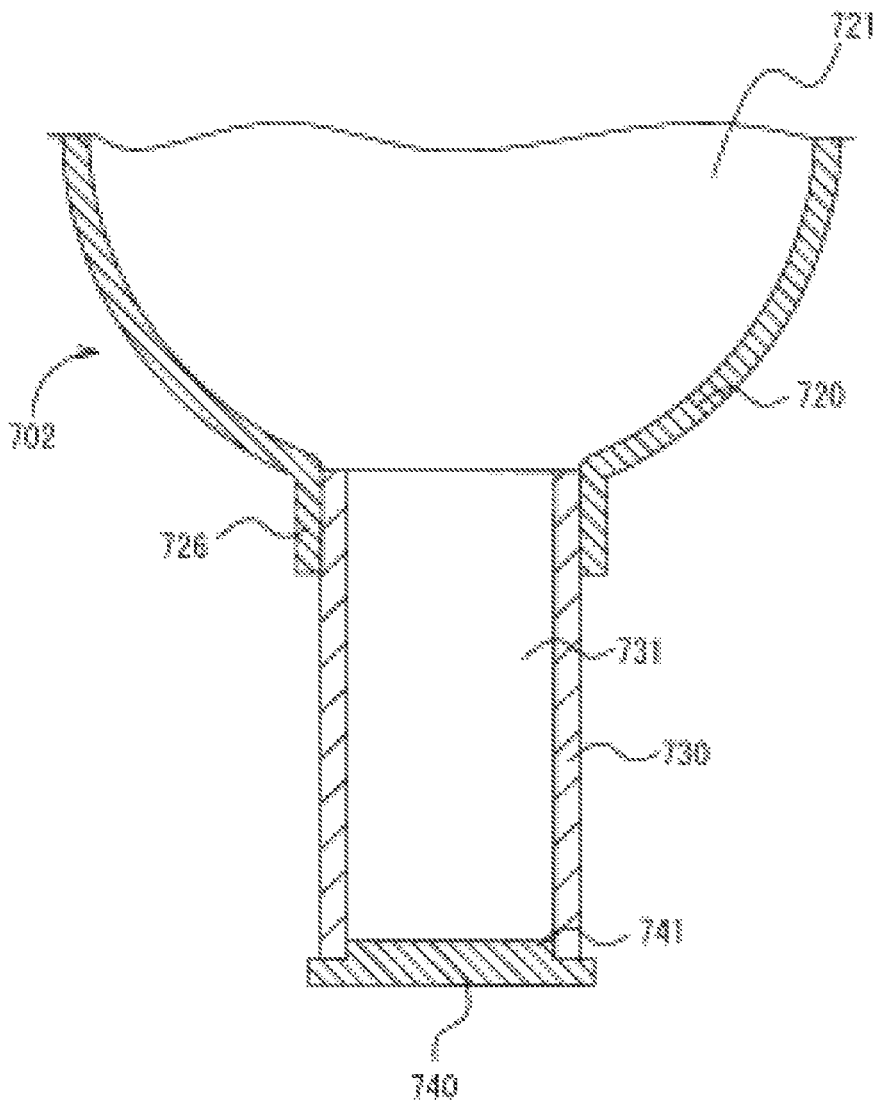
FIG. 20 is a cross-sectional view showing an example of the state in which a second accommodating part 730 is attached to a first accommodating part 720.

FIG. 20 is a cross-sectional view showing an example of the state in which the second accommodating part 730 is attached to the first accommodating part 720. In the present embodiment, the second accommodating part 730 is attached to the first accommodating part 720 in a detachable manner. In other words, the second accommodating part 730 and the first accommodating part 720 are separate members. In such case, as compared to the case in which the second accommodating part and the first accommodating part are integrally molded, the length of the second accommodating part 730 in the axial direction can be made longer, and thus, it can be assured that the blood cells will be accommodated, even when the amount thereof is large. When the first accommodating part and the second accommodating part are integrally molded by injection molding, etc., it is difficult to appropriately form the second accommodating part which is elongated in the axial direction. This is due to the fact that, while the integral molding is implemented using a mold, stress concentration is likely to occur at the location where the second accommodating part having a small inner diameter is molded, during molding using a mold, and thus there is a risk that the second accommodating part may break.

The second accommodating part 730 is press-fitted into and attached to a to-be-attached part 726, which is an opening part of the first accommodating part 720 located on the side of the second accommodating part 730. In this manner, the connecting parts of the second accommodating part 730 and the first accommodating part 720 are closely attached together after attachment, and thus, evaporation of the blood from the connecting parts of the first accommodating part 720 and the second accommodating part 730, being separate members, can be prevented.

In addition, the present embodiment is configured such that different types of second accommodating parts 730 may be attached to the first accommodating part 720. In particular, an accommodating part selected from a small-diameter accommodating part and a large-diameter accommodating part, each of which having a different inner diameter as shown in FIG. 21, may be attached, as the second accommodating part 730, to the first accommodating part 720. Here, two accommodating parts are described as examples; however, the present invention is not limited thereto, and one accommodating part selected from, for example, three or more accommodating parts having different inner diameters may be attached to the first accommodating part 720.

Figure 21A:
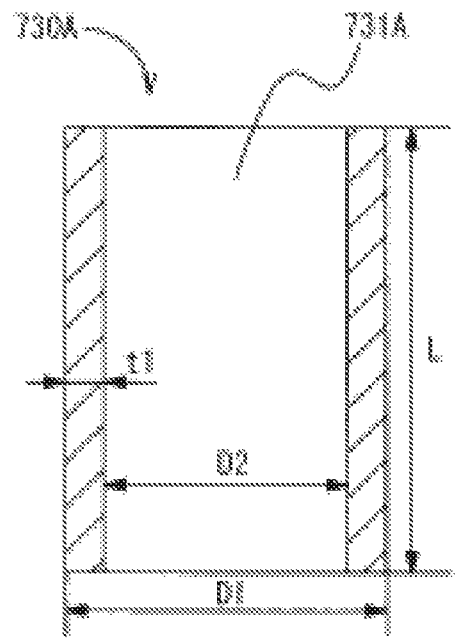
FIG. 21A contains diagrams for explaining examples of a small-diameter accommodating part and a large-diameter accommodating part.
Figure 21B:
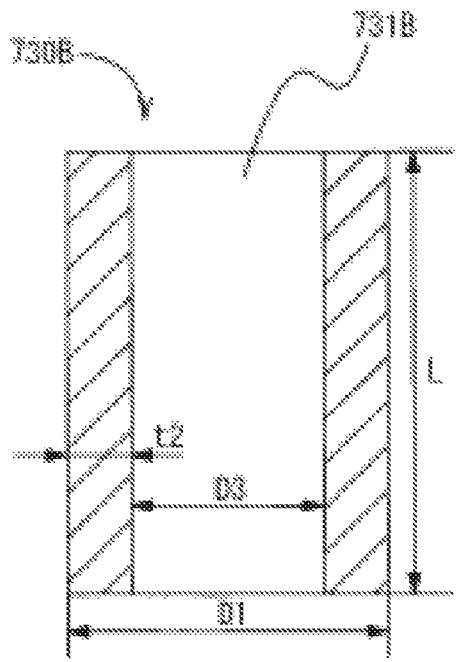
FIG. 21B contains diagrams for explaining examples of a small-diameter accommodating part and a large-diameter accommodating part.

FIG. 21 contains diagrams for explaining examples of a small-diameter accommodating part and a large-diameter accommodating part. FIG. 21(a) shows a large-diameter accommodating part 730A, and FIG. 21(b) shows a small-diameter accommodating part 730B. The large-diameter accommodating part 730A and the small-diameter accommodating part 730B respectively include a large-diameter cavity part 731A and a small-diameter cavity part 731B for accommodating blood therein.

The inner diameter D2 of the large-diameter accommodating part 730A is larger than the inner diameter D3 of the small-diameter accommodating part 730B. On the other hand, the lengths L of the large-diameter accommodating part 730A and the small-diameter accommodating part 730B in the axial direction have the same size. Accordingly, the amount of blood that can be accommodated in the large-diameter accommodating part 730A (the large-diameter cavity part 731A) is larger than the amount of blood that can be accommodated in the small-diameter accommodating part 730B (the small-diameter cavity part 731B). In other words, after centrifugal separation, the amount of blood cells that can be accommodated in the large-diameter accommodating part 730A is larger than the amount of blood cells that can be accommodated in the small-diameter accommodating part 730B. Thus, the large-diameter accommodating part 730A or the small-diameter accommodating part 730B may be attached, depending on the amount of blood cells needed for examinations, and thus, the blood plasma and the blood cells can be respectively accommodated, in an appropriate manner, in the first accommodating part and the second accommodating part after centrifugal separation.

The outer diameter D1 of the large-diameter accommodating part 730A may have the same size as the outer diameter D1 of the small-diameter accommodating part 730B. In particular, as shown in FIG. 21, by reducing the thickness t1 of the large-diameter accommodating part 730A to a thickness smaller than the thickness t2 of the small-diameter accommodating part 730B, the outer diameter of the large-diameter accommodating part 730A and the outer diameter of the small-diameter accommodating part 730B can be made to have the same size. In such case, the large-diameter accommodating part 730A and the small-diameter accommodating part 730B can be press-fitted into and attached to the to-be-attached part 726 (FIG. 20) of the first accommodating part 720, without altering the configuration of the to-be-attached part 726.

In the above, it has been described that outer diameters D1 of the large-diameter accommodating part 730A and the small-diameter accommodating part 730B have the same size; however, the present invention is not limited thereto. For example, the outer diameter of the large-diameter accommodating part 730A may be larger than the outer diameter of the small-diameter accommodating part 730B.

In addition, in the above, it has been described that the lengths L of the large-diameter accommodating part 730A and the small-diameter accommodating part 730B in the axial direction have the same size; however, the present invention is not limited thereto. For example, the length of the large-diameter accommodating part 730A in the axial direction may be larger than the length of the small-diameter accommodating part 730B in the axial direction. In such case, the amount of blood cells that can be accommodated may be changed depending on the second accommodating part to be attached.

Moreover, in the above, it has been described that the second accommodating part 730 is press-fitted into and attached to the first accommodating part 720; however, the present invention is not limited thereto. For example, the first accommodating part 720 may be configured such that it is press-fitted into and attached to the second accommodating part 730. Additionally, a member for fixing the second accommodating part 730 to the first accommodating part 720 may be separately provided. In short, any configuration may be employed as long as the second accommodating part 730 is closely attached to the first accommodating part 720.

In the present embodiment, when the blood in the inner container 702 is subjected to centrifugal separation, blood cells having a higher specific gravity are accommodated in the second accommodating part 730 on the lower side and blood plasma having a lower specific gravity is accommodated in the first accommodating part 720 on the upper side. In this way, when the blood plasma and the blood cells are accommodated in different accommodating parts after centrifugal separation, the blood plasma and the blood cells can be easily taken out individually. For example, it is possible to easily take out only the blood cells which are positioned on the side closer to the bottom part of the inner container 702 than the blood plasma after centrifugal separation, without using a micropipette, by way of removing the second accommodating part 730 having the blood cells accommodated therein from the inner container 702. In addition, when the second accommodating part 730 is removed, the blood plasma can also be appropriately taken out since the blood plasma does not get mixed with the blood cells when the blood plasma is discharged from the opening in the to-be-attached part 726 or when the blood plasma is taken out with a micropipette.

The second accommodating part 730 may be made of a material harder than the first accommodating part 720, which is made of ABS resin or the like, as described above. For example, the second accommodating part 730 is made of glass, hard polycarbonate, or the like. In such case, since the second accommodating part 730 has high rigidity, the second accommodating part 730 may be easily inserted into the to-be-attached part 726 of the first accommodating part 720 when the second accommodating part 730 is to be press-fitted into the first accommodating part 720, and thus, the second accommodating part 730 may be easily attached to the to-be-attached part 726.

The first accommodating part 720 may be made of a material having flexibility. In such case, the to-be-attached part 726 of the first accommodating part 720 easily expands by being pressed by the second accommodating part 730 when the second accommodating part 730 is to be press-fitted into the first accommodating part 720, and thus, second accommodating part 730 is easily attached to the to-be-attached part 726.

As shown in FIG. 20, the lower lid part 740 obstructs an opening of the second accommodating part 730, which is positioned on the opposite side from the side where the second accommodating part 730 is attached to the first accommodating part 720. The lower lid part 740 functions as a stopper that prevents the blood (blood cells after centrifugal separation) accommodated in the second accommodating part 730 from leaking. The lower lid part 740 is attached to the second accommodating part 730 in a detachable manner. For example, a convex part 741 is press-fitted into and attached to the second accommodating part 730 such that the lower lid part 740 is closely attached to the second accommodating part 730.

It should be noted that the lower lid part 740 may also be a lid formed with a concave part (not shown), serving as a liquid pool, in the surface on the side of the second cavity part 731. When a medical agent (for example, a washing solution) is accommodated in the inner container 702, such medical agent collects in the liquid pool. In addition, the blood cells after centrifugal separation are also accommodated in the concave part, and thus, the capacity of the second accommodating part 730 may be increased.

The first accommodating part 720 and the second accommodating part 730 may also accommodate a separating agent. The separating agent is accommodated in the inner container 702 together with blood before centrifugal separation. The separating agent exhibits so-called thixoropy. Thixoropy is a property exhibited by a substance that is an intermediate of a plastic solid, such as gel, and a non-Newtonian liquid, such as sol. Such separating agent changes from a gel-like phase to a liquid phase and moves to a position between the blood cell part and the blood plasma part during centrifugal separation, and then returns to the gel-like phase again after centrifugal separation. Accordingly, the separating agent can keep the blood plasma accommodated in the first accommodating part 720 and the blood cells accommodated in the second accommodating part 730 in an isolated state.

Figure 22:
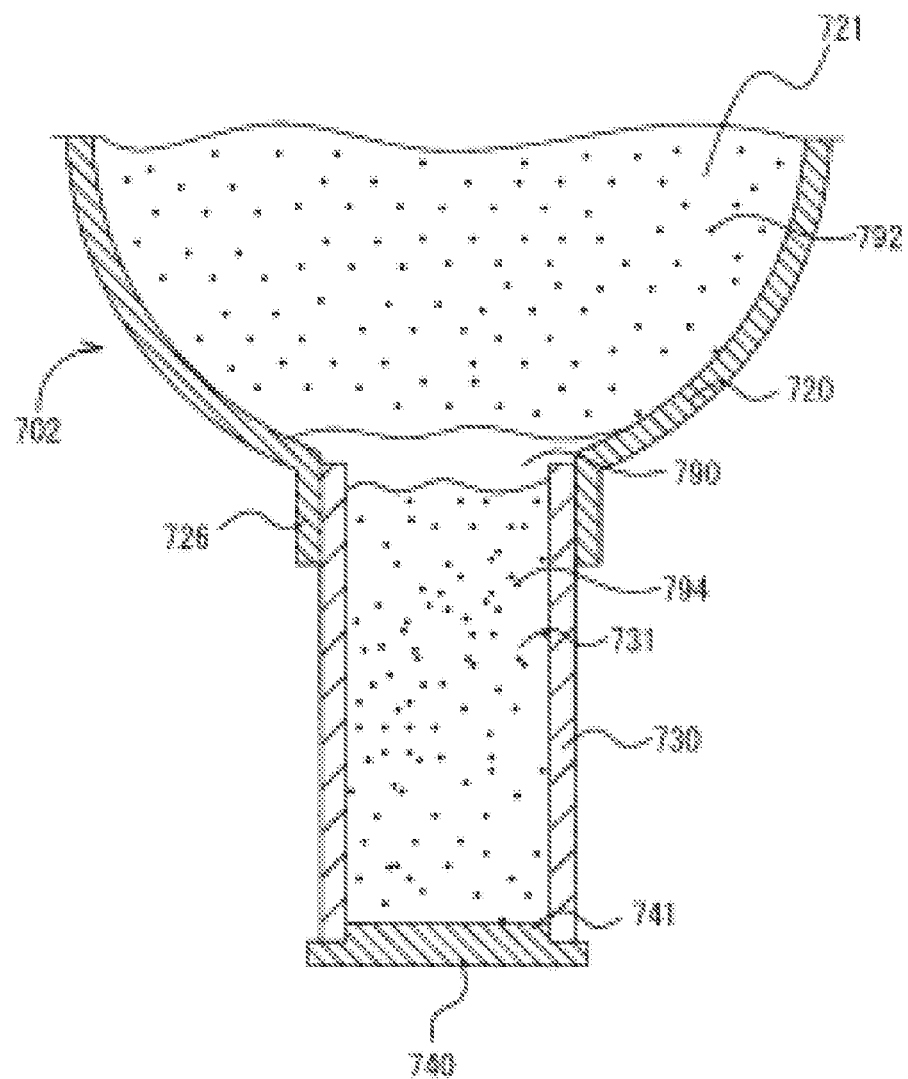
FIG. 22 is a schematic diagram showing an example of the state of blood and a separating agent within the inner container 702 after centrifugal separation.

FIG. 22 is a schematic diagram showing an example of the state of the blood and the separating agent within the inner container 702 after centrifugal separation. When the blood is subjected to centrifugal separation, the separating agent (the separating agent 790 shown in FIG. 22) is positioned at a position connecting the first cavity part 721 and the second cavity part 731. In such case, the blood plasma is accommodated only in the first cavity part 721 and the blood cells are accommodated only in the second cavity part 731 after centrifugal separation, and thus, the blood plasma and the blood cells can be easily taken out individually thereafter. More specifically, it is possible to take out only the blood cells by removing the second accommodating part 730.

In addition, since the separating agent possesses the above-described thixoropy, it does not outflow from the opening in the to-be-attached part 726, even when the second accommodating part 730 is removed after centrifugal separation. Moreover, since the separating agent fills the opening in the to-be-attached part 726, the blood plasma accommodated in the first accommodating part 720 does not outflow from the opening in the to-be-attached part 726 either. In short, the separating agent functions as a stopper.
(Example of the Flow from Blood Sampling to Examination Thereof)

Centrifugal separation of blood by means of a centrifuge has conventionally been carried out in analysis agencies where examinations and analyses are performed. However, the centrifuges in the analysis agencies are expensive and so are the running costs thereof, and cost reduction has therefore been requested.

In response to such request, if the bodily fluid container 700 having the above-described configuration is used, it is possible to provide a service in which centrifugal separation of blood is carried out with an inexpensive centrifuge at facilities (for example, a drug store, etc.) other than the analysis agencies and then, the examination and analysis are carried out in the analysis agency. In this manner, the usage of centrifuges in analysis agencies can be reduced and thus, the running costs can also be reduced. An example of the flow of such service will be described with reference to FIG. 23.

Figure 23:
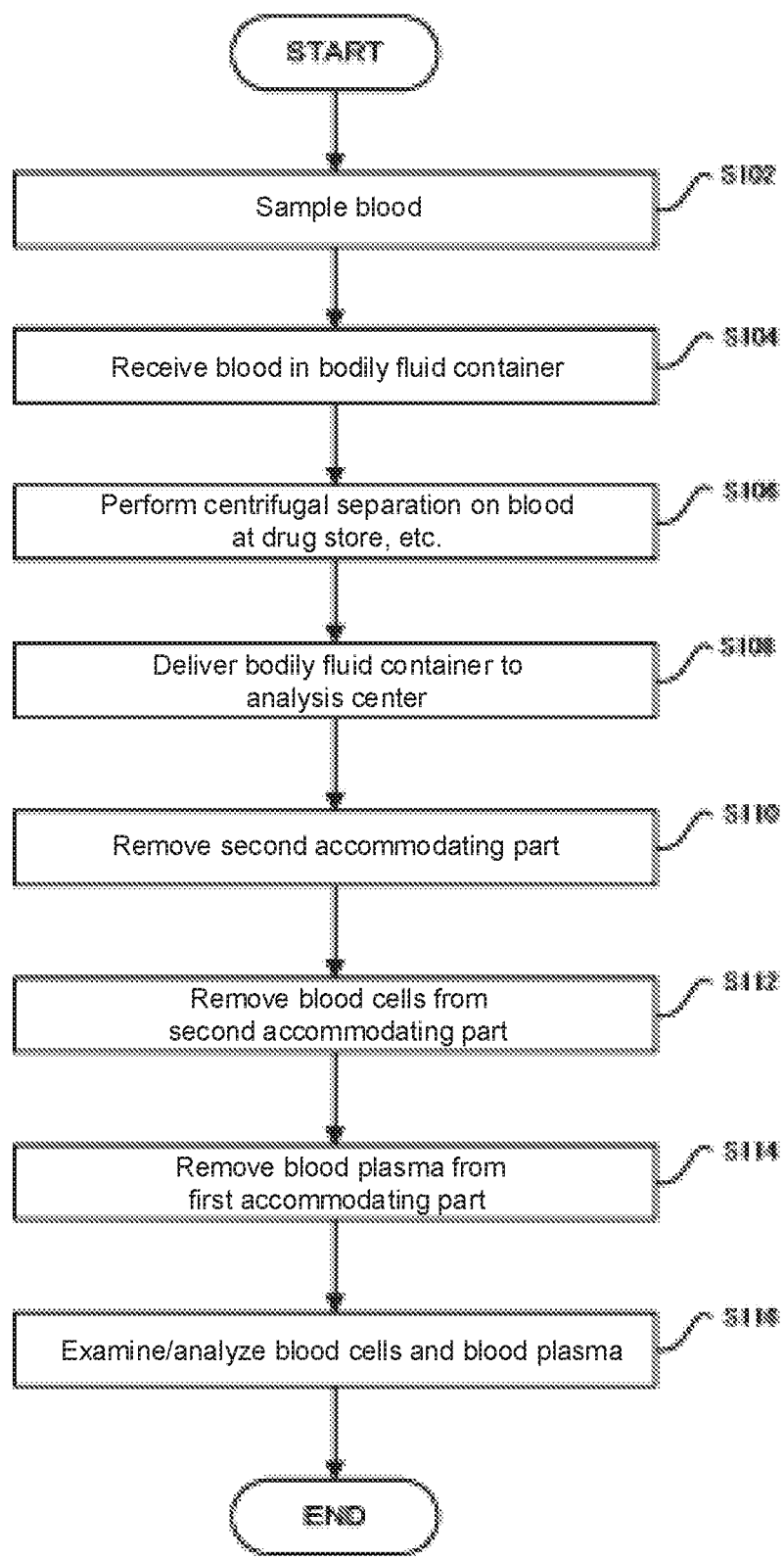
FIG. 23 is a flow diagram illustrating an example of the flow from blood sampling to examination thereof.

FIG. 23 is a flow diagram illustrating an example of the flow from blood sampling to examination thereof. In the present service, a user who desires to receive a blood examination receives the bodily fluid sampler 600 at a drug store, etc. and performs blood sampling (step S102). More specifically, the user sucks the blood, being the sampling target, by means of the suction part 601 of the bodily fluid sampler 600.

Next, the user or a store staff, or the like, of the drug store discharges the blood in the bodily fluid sampler 600 into the bodily fluid container 700 (step S104). More specifically, the store staff, or the like, presses the pressure generating part 604 of the bodily fluid sampler 600 in the state in which the bodily fluid sampler 600 is inserted into the bodily fluid container 700 (more specifically, the inner container 702), thereby causing the blood accumulated in the suction part 601 to be discharged into the bodily fluid container 700. Here, a separating agent is also placed into the bodily fluid container 700 before or after discharge of blood into the bodily fluid container 700.

Next, the store staff sets the bodily fluid container 700 in a centrifuge installed at the drug store and performs centrifugal separation of the blood accommodated in the bodily fluid container 700 (step S106). The conditions, such as rotating speed, at the time of performing centrifugal separation are predetermined. When centrifugal separation is performed, blood cells and blood plasma are respectively accommodated in the second accommodating part 730 and the first accommodating part 720, for example, as shown in FIG. 22, due to the difference in specific gravity between the blood cells and blood plasma in blood. It should be noted that the centrifugal separation may be performed in the state in which the outer container 701 having the inner container 702 received therein is set onto the centrifuge or in the state in which only the inner container 702 is set onto the centrifuge.

The bodily fluid container 700, after centrifugal separation, is delivered to an analysis agency where the examination and analysis of the blood are carried out (step S108). Then, the second accommodating part 730 attached to the first accommodating part 720 is removed at the analysis agency (step S110). More specifically, the press-fitted second accommodating part 730 is removed by being pulled out in the direction reverse to the attaching direction.

Next, the blood cells are taken out from the second accommodating part 730 (step S112). More specifically, first, the lower lid part 740 that obstructs the lower opening is removed from the second accommodating part 730. Then, the blood cells accommodated in the second accommodating part 730 are discharged through the lower opening. In this way, it is possible to take out only the blood cells separately, without using instruments such as a micropipette or the like.

Next, the blood plasma is taken out from the first accommodating part 720 (step S114). More specifically, first, the upper lid part 722 that obstructs the upper opening is opened. Then, an instrument, such as a micropipette, or the like, is inserted from the upper opening to suck and take out the blood plasma. It should be noted that the blood plasma may also be discharged from the opening in the to-be-attached part in the first accommodating part 720. In such case, the micropipette is not required.

Next, the analysis agency performs examinations and analyses on the blood plasma and the blood cells that are taken out (step S116). Thus, the health conditions of the user, whose blood was sampled, can be determined.

In the above-described service, even a drug store staff, or the like, who is unfamiliar with centrifugal separation, or the like, of blood, can easily set the bodily fluid container 700 onto the centrifuge and can easily know whether the centrifugal separation was performed appropriately. Accordingly, centrifugal separation of blood, which has to date only been performed in analysis agencies, can be performed at a drug store, or the like.
(Effect of Third Embodiment)

As has been described above, the bodily fluid container 700 according to the present embodiment is provided with, as shown in FIG. 20: the second accommodating part 730 having the second cavity part 731 that receives therein a bodily fluid (in particular, blood) together with the first cavity part 721; and the lower lid part 740 that obstructs the opening located on the opposite side from the side where the second accommodating part 730 is attached to the first accommodating part 720. The second accommodating part 730 is attached to the first accommodating part 720 in a detachable manner, and the inner diameter of the second cavity part 731 is smaller than the inner diameter of the first cavity part 721.

In such case, as compared to the case in which the second accommodating part and the first accommodating part are integrally molded, the length of the second accommodating part 730 in the axial direction can be made larger, and thus, it can be assured that the blood cells will be accommodated in the second accommodating part 730, even when the amount thereof is large. Then, the blood cells within the blood can be easily taken out by removing the second accommodating part 730 from the first accommodating part 720 and by opening the lower lid part 740. In particular, workability is significantly improved as compared to the conventional case in which the blood cells are sucked and taken out by means of a micropipette, or the like.

In the above, it has been described that the bodily fluid container 700 is configured by the inner container 702 accommodating blood and the outer container 701 accommodating the inner container 702; however, the bodily fluid container 700 is not limited thereto. For example, the bodily fluid container 700 may be configured by the inner container 702 only, and it may not need to include the outer container.

Moreover, in the above, the description has been given using blood as an example of the bodily fluid; however, the bodily fluid is not limited thereto. For example, the bodily fluid may be urine. In such case, blood cells, or the like, of urine are accommodated in the second accommodating part 730 after centrifugal separation, and thus, the blood cells of the urine can be easily taken out.

Furthermore, in the above, it has been described that the blood accumulated in the suction part 601 of the bodily fluid sampler 600 is discharged into the bodily fluid container 700 and then centrifugal separation is performed; however, the present invention is not limited thereto. For example, the suction part 601 and the blocking part 603 may be removed (in particular, the suction part 601 may be broken off from the main body part 602 at the section of the blocking part 603) and attached to the inner container 702 of the bodily fluid container 700, and then centrifugal separation may be performed. In such case, the inner wall of the inner container 702 may be formed in line with the shape of the main body part 602 and the blocking part 603 such that the main body part 602 and the blocking part 603 may be easily attached. In addition, a configuration for holding the attached suction part 601 and the blocking part 603 may be provided to the upper lid part 722 of the inner container 702.

According to the above-described configuration, a store staff, or the like, is protected from touching blood and also blood is prevented from being exposed to the air. Moreover, as compared to the case in which blood is discharged into the bodily fluid container 700 by causing gas to flow through the ventilation channels 621 by means of pressure generated by the pressure generating part 604, the above-described configuration can discharge blood, without leakage, by way of centrifugal separation from the suction part 601 attached to the inner container 702, and thus, is efficient. In addition, the suction part 601 and the blocking part 603 can be easily removed after centrifugal separation by opening the upper lid part 722.

Accordingly, the invention has been described by way of the embodiments; however, the technical scope of the present invention is not limited to the scope described in the above-described embodiments. It is obvious to those skilled in the art that various alterations or modifications can be made to the above-described embodiments. It is clear from the descriptions in the claims that the embodiments with such alterations or modifications still fall under the technical scope of the present invention.

DESCRIPTIONS OF REFERENCE NUMBERS 1 suction part
2 main body part
3 blocking part
4 pressure generating part
11 suction port
12 suction plate
13 accumulation part
21 ventilation channel
22 coupling part
31 opening part
41 opening
100 bodily fluid sampler
200 bodily fluid sampler
300 bodily fluid sampler
500 bodily fluid container
501 outer container
502 inner container
510 outer accommodating part
511 outer cavity part
512 outer lid part
513 fixing part
514 outer coupling part
520 inner accommodating part
521 inner cavity part
522 inner lid part
522a first inner lid part
523 projection part
524 inner coupling part
700 bodily fluid container
701 outer container
702 inner container
720 first accommodating part
721 first cavity part
726 to-be-attached part
730 second accommodating part
730A large-diameter accommodating part
730B small-diameter accommodating part
731 second cavity part
740 lower lid part
1000 bodily fluid sampling device
2000 bodily fluid sampling device

What is claimed is:

1. A bodily fluid sampler for sampling a bodily fluid, the bodily fluid sampler comprising:
    a suction part comprising a suction port, wherein the suction port comprises an accumulation part and a step formed on an inner surface of the suction port at a position where the suction part and a blocking part make contact with each other;
    a main body part comprising a ventilation channel that allows gas for discharging the bodily fluid to run therethrough toward the suction part; and
    the blocking part comprising a tapered cavity having a first inner diameter on a side of the suction part smaller than a second inner diameter at the step of the suction port, wherein the blocking part is detachably disposed between the main body part and the suction part,
    wherein a head of the suction part is immersed in the bodily fluid, bodily fluid is sucked into the suction port due to capillarity, and accumulated in the accumulation part, and
    wherein the bodily fluid continues to flow in until a stress generated by a difference between the first inner diameter and the second inner diameter is larger than the pressure generated by capillarity, preventing bodily fluid from flowing into the main body part.

2. The bodily fluid sampler according to claim 1, wherein the ventilation channel has a tapered form in which an inner diameter thereof decreases as the distance to the blocking part decreases.

3. The bodily fluid sampler according to claim 1, wherein the ventilation channel has a smallest inner diameter at a surface where the main body part and the blocking part make contact with each other.

4. The bodily fluid sampler according to claim 1, wherein an inner diameter of the ventilation channel has a size equal to or larger than that of an inner diameter of an opening part of the blocking part at a surface where the main body part and the blocking part make contact with each other.

5. The bodily fluid sampler according to claim 1, wherein an outer diameter of the blocking part is smaller than an inner diameter of the suction part at a position where the suction part makes contact with the main body part, and the blocking part is provided on an inner side of the suction part.

6. The bodily fluid sampler according to claim 5, wherein the suction part is connected to the main body part, in a detachable manner, in the state in which the blocking part is provided on the inner side of the suction part.

* * * * *